(12) United States Patent
Lautenbach et al.

(10) Patent No.: US 9,539,200 B2
(45) Date of Patent: *Jan. 10, 2017

(54) TWO-PIECE, INTERNAL-CHANNEL OSMOTIC DELIVERY SYSTEM FLOW MODULATOR

(71) Applicant: Intarcia Therapeutics Inc., Boston, MA (US)

(72) Inventors: Scott C. Lautenbach, San Mateo, CA (US); Pedro E. De La Serna, San Jose, CA (US); Pauline C. Zamora, Sausalito, CA (US); Michael A. Desjardin, Aptos, CA (US)

(73) Assignee: Intarcia Therapeutics Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/632,700

(22) Filed: Feb. 26, 2015

(65) Prior Publication Data

US 2015/0231062 A1    Aug. 20, 2015

Related U.S. Application Data

(60) Continuation of application No. 13/898,358, filed on May 20, 2013, now Pat. No. 8,992,962, which is a
(Continued)

(51) Int. Cl.
*A61K 9/00* (2006.01)

(52) U.S. Cl.
CPC ........ *A61K 9/0004* (2013.01); *Y10T 29/49236* (2015.01)

(58) Field of Classification Search
CPC .. A61K 9/0004; A61K 9/0024; A61K 9/2866; A61K 9/2054; A61L 31/10; A61L 31/16; A61L 27/54; A61M 5/31513; A61M 5/31515; A61M 5/31511; A61M 31/002; A61M 2005/14513; Y10T 29/49236
See application file for complete search history.

(56) References Cited

U.S. PATENT DOCUMENTS 2,110,208 A   3/1938  Eggert
2,168,437 A   8/1939  Buercklin
(Continued)

FOREIGN PATENT DOCUMENTS

EP    0079405    5/1983
EP    0254394    1/1988
(Continued)

OTHER PUBLICATIONS

International Search Report and Written Opinion for International Application No. PCT/US2004/010107, mailed Nov. 4, 2004.
(Continued)

*Primary Examiner* — Blessing M Fubara
(74) *Attorney, Agent, or Firm* — Cooley LLP

(57) ABSTRACT

An osmotic delivery system flow modulator includes an outer shell constructed and arranged for positioning in an opening, an inner core inserted in the outer shell, and a fluid channel having a spiral shape defined between the outer shell and the inner core. The fluid channel is adapted for delivery of an active agent formulation from the reservoir of the osmotic delivery system.

24 Claims, 5 Drawing Sheets

Related U.S. Application Data continuation of application No. 13/740,187, filed on Jan. 12, 2013, now Pat. No. 8,470,353, which is a continuation of application No. 13/601,939, filed on Aug. 31, 2012, now Pat. No. 8,367,095, which is a continuation of application No. 13/433,287, filed on Mar. 29, 2012, now Pat. No. 8,273,365, which is a continuation of application No. 13/209,328, filed on Aug. 12, 2011, now Pat. No. 8,158,150, which is a division of application No. 11/755,494, filed on May 30, 2007, now Pat. No. 8,052,996, and a continuation-in-part of application No. 11/347,562, filed on Feb. 3, 2006, now Pat. No. 8,114,437.

(60) Provisional application No. 60/809,451, filed on May 30, 2006, provisional application No. 60/650,225, filed on Feb. 3, 2005.

(56) References Cited

U.S. PATENT DOCUMENTS

| | | | |
|---|---|---|---|
| 3,025,991 | A | 3/1962 | Gillon |
| 3,122,162 | A | 2/1964 | Sands |
| 3,625,214 | A | 12/1971 | Higuchi |
| 3,632,768 | A | 1/1972 | Bergy et al. |
| 3,732,865 | A | 5/1973 | Higuchi et al. |
| 3,797,492 | A | 3/1974 | Place |
| 3,869,549 | A | 3/1975 | Geller |
| 3,987,790 | A | 10/1976 | Eckenhoff et al. |
| 3,995,631 | A | 12/1976 | Higuchi et al. |
| 3,995,632 | A | 12/1976 | Nakano et al. |
| 4,008,719 | A | 2/1977 | Theeuwes et al. |
| 4,034,756 | A | 7/1977 | Higuchi et al. |
| 4,078,060 | A | 3/1978 | Benson et al. |
| 4,111,201 | A | 9/1978 | Theeuwes |
| 4,111,202 | A | 9/1978 | Theeuwes |
| 4,211,771 | A | 7/1980 | Witkowski et al. |
| 4,243,030 | A | 1/1981 | Lynch et al. |
| 4,305,927 | A | 12/1981 | Theeuwes et al. |
| 4,310,516 | A | 1/1982 | Chang et al. |
| 4,340,054 | A | 7/1982 | Michaels |
| 4,350,271 | A | 9/1982 | Eckenhoff |
| 4,373,527 | A | 2/1983 | Fischell |
| 4,376,118 | A | 3/1983 | Daher et al. |
| 4,439,196 | A | 3/1984 | Higuchi |
| 4,455,143 | A | 6/1984 | Theeuwes et al. |
| 4,455,145 | A | 6/1984 | Theeuwes |
| 4,552,561 | A | 11/1985 | Eckenhoff et al. |
| 4,588,614 | A | 5/1986 | Lauchenauer |
| 4,594,108 | A | 6/1986 | Greminger, Jr. et al. |
| 4,609,374 | A | 9/1986 | Ayer |
| 4,639,244 | A | 1/1987 | Rizk et al. |
| 4,655,462 | A | 4/1987 | Balsells |
| 4,673,405 | A | 6/1987 | Guittard et al. |
| 4,675,184 | A | 6/1987 | Hasegawa et al. |
| 4,695,623 | A | 9/1987 | Stabinsky |
| 4,727,138 | A | 2/1988 | Goeddel et al. |
| 4,734,284 | A | 3/1988 | Terada et al. |
| 4,743,449 | A | 5/1988 | Yoshida et al. |
| 4,753,651 | A | 6/1988 | Eckenhoff |
| 4,762,791 | A | 8/1988 | Goeddel et al. |
| 4,765,989 | A | 8/1988 | Wong et al. |
| 4,783,337 | A | 11/1988 | Wong et al. |
| 4,820,638 | A | 4/1989 | Swetly et al. |
| 4,826,144 | A | 5/1989 | Balsells |
| 4,830,344 | A | 5/1989 | Balsells |
| 4,845,196 | A | 7/1989 | Cowling |
| 4,847,079 | A | 7/1989 | Kwan |
| 4,851,228 | A | 7/1989 | Zentner et al. |
| 4,865,845 | A | 9/1989 | Eckenhoff et al. |
| 4,873,080 | A | 10/1989 | Brickl et al. |
| 4,874,388 | A | 10/1989 | Wong et al. |
| 4,876,781 | A | 10/1989 | Balsells |
| 4,885,166 | A | 12/1989 | Meyer et al. |
| 4,886,668 | A | 12/1989 | Haslam et al. |
| 4,892,778 | A | 1/1990 | Theeuwes et al. |
| 4,893,795 | A | 1/1990 | Balsells |
| 4,897,471 | A | 1/1990 | Stabinsky |
| 4,907,788 | A | 3/1990 | Balsells |
| 4,915,366 | A | 4/1990 | Balsells |
| 4,915,949 | A | 4/1990 | Wong et al. |
| 4,915,954 | A | 4/1990 | Ayer et al. |
| 4,917,887 | A | 4/1990 | Hauptmann et al. |
| 4,917,895 | A | 4/1990 | Lee et al. |
| 4,927,687 | A | 5/1990 | Nuwayser |
| 4,929,554 | A | 5/1990 | Goeddel et al. |
| 4,931,285 | A | 6/1990 | Edgren et al. |
| 4,934,666 | A | 6/1990 | Balsells |
| 4,940,465 | A | 7/1990 | Theeuwes et al. |
| 4,952,402 | A | 8/1990 | Sparks et al. |
| 4,961,253 | A | 10/1990 | Balsells |
| 4,964,204 | A | 10/1990 | Balsells |
| 4,969,884 | A | 11/1990 | Yum |
| 4,974,821 | A | 12/1990 | Balsells |
| 4,976,966 | A | 12/1990 | Theeuwes et al. |
| 5,004,689 | A | 4/1991 | Fiers et al. |
| 5,006,346 | A | 4/1991 | Theeuwes et al. |
| 5,019,382 | A | 5/1991 | Cummins, Jr. |
| 5,023,088 | A | 6/1991 | Wong et al. |
| 5,024,842 | A | 6/1991 | Edgren et al. |
| 5,030,216 | A | 7/1991 | Theeuwes et al. |
| 5,034,229 | A | 7/1991 | Magruder et al. |
| 5,057,318 | A | 10/1991 | Magruder et al. |
| 5,059,423 | A | 10/1991 | Magruder et al. |
| 5,071,642 | A | 12/1991 | Lahr et al. |
| 5,072,070 | A | 12/1991 | Balsells |
| 5,079,388 | A | 1/1992 | Balsells |
| 5,091,188 | A | 2/1992 | Haynes |
| 5,108,078 | A | 4/1992 | Balsells |
| 5,110,596 | A | 5/1992 | Magruder et al. |
| 5,112,614 | A | 5/1992 | Magruder et al. |
| 5,113,938 | A | 5/1992 | Clayton |
| 5,117,066 | A | 5/1992 | Balsells |
| 5,118,666 | A | 6/1992 | Habener |
| 5,120,306 | A | 6/1992 | Gosselin |
| 5,120,712 | A | 6/1992 | Habener |
| 5,120,832 | A | 6/1992 | Goeddel et al. |
| 5,122,128 | A | 6/1992 | Cardinal et al. |
| 5,126,142 | A | 6/1992 | Ayer et al. |
| 5,134,244 | A | 7/1992 | Balsells |
| 5,137,727 | A | 8/1992 | Eckenhoff |
| 5,151,093 | A | 9/1992 | Theeuwes et al. |
| 5,160,122 | A | 11/1992 | Balsells |
| 5,160,743 | A | 11/1992 | Edgren et al. |
| 5,161,806 | A | 11/1992 | Balsells |
| 5,180,591 | A | 1/1993 | Magruder et al. |
| 5,190,765 | A | 3/1993 | Jao et al. |
| 5,203,849 | A | 4/1993 | Balsells |
| 5,207,752 | A | 5/1993 | Sorenson et al. |
| 5,209,746 | A | 5/1993 | Balaban et al. |
| 5,213,809 | A | 5/1993 | Wright et al. |
| 5,219,572 | A | 6/1993 | Sivaramakrishnan |
| 5,221,278 | A | 6/1993 | Linkwitz et al. |
| 5,223,265 | A | 6/1993 | Wong |
| 5,231,176 | A | 7/1993 | Goeddel et al. |
| 5,234,424 | A | 8/1993 | Yum et al. |
| 5,234,692 | A | 8/1993 | Magruder et al. |
| 5,234,693 | A | 8/1993 | Magruder et al. |
| 5,234,695 | A | 8/1993 | Hobbs et al. |
| 5,252,338 | A | 10/1993 | Jao et al. |
| 5,260,069 | A | 11/1993 | Chen |
| 5,278,151 | A | 1/1994 | Korb et al. |
| 5,279,608 | A | 1/1994 | Cherif Cheikh |
| 5,284,655 | A | 2/1994 | Bogdansky et al. |
| 5,290,271 | A | 3/1994 | Jernberg |
| 5,300,302 | A | 4/1994 | Tachon et al. |
| 5,308,348 | A | 5/1994 | Balaban et al. |
| 5,312,389 | A | 5/1994 | Theeuwes et al. |
| 5,312,390 | A | 5/1994 | Wong |
| 5,318,558 | A | 6/1994 | Linkwitz et al. |
| 5,318,780 | A | 6/1994 | Viegas et al. |
| 5,320,616 | A | 6/1994 | Magruder et al. |
| 5,324,280 | A | 6/1994 | Wong et al. |

(56) References Cited

U.S. PATENT DOCUMENTS

| | | |
|---|---|---|
| 5,336,057 A | 8/1994 | Fukuda et al. |
| 5,352,662 A | 10/1994 | Brooks et al. |
| 5,368,588 A | 11/1994 | Bettinger |
| 5,368,863 A | 11/1994 | Eckenhoff et al. |
| 5,371,089 A | 12/1994 | Rattan |
| 5,374,620 A | 12/1994 | Clark et al. |
| 5,385,738 A | 1/1995 | Yamahira et al. |
| 5,411,951 A | 5/1995 | Mitchell |
| 5,413,572 A | 5/1995 | Wong et al. |
| 5,413,672 A | 5/1995 | Hirotsuji et al. |
| 5,424,286 A | 6/1995 | Eng |
| 5,429,602 A | 7/1995 | Hauser |
| 5,443,459 A | 8/1995 | Wong et al. |
| 5,445,829 A | 8/1995 | Paradissis et al. |
| 5,456,679 A | 10/1995 | Balaban et al. |
| 5,458,888 A | 10/1995 | Chen |
| 5,464,929 A | 11/1995 | Bezwada et al. |
| 5,472,708 A | 12/1995 | Chen |
| 5,486,365 A | 1/1996 | Takado et al. |
| 5,498,255 A | 3/1996 | Wong et al. |
| 5,511,355 A | 4/1996 | Dingler |
| 5,512,293 A | 4/1996 | Landrau et al. |
| 5,512,549 A | 4/1996 | Chen et al. |
| 5,514,110 A | 5/1996 | Teh |
| 5,529,914 A | 6/1996 | Hubbell et al. |
| 5,531,736 A | 7/1996 | Wong et al. |
| 5,540,665 A | 7/1996 | Mercado et al. |
| 5,540,912 A | 7/1996 | Roorda et al. |
| 5,543,156 A | 8/1996 | Roorda et al. |
| 5,545,618 A | 8/1996 | Buckley et al. |
| 5,557,318 A | 9/1996 | Gabriel |
| 5,571,525 A | 11/1996 | Roorda et al. |
| 5,574,008 A | 11/1996 | Johnson et al. |
| 5,574,137 A | 11/1996 | Gray et al. |
| 5,580,578 A | 12/1996 | Oshlack et al. |
| 5,595,751 A | 1/1997 | Bezwada |
| 5,595,759 A | 1/1997 | Wright et al. |
| 5,597,579 A | 1/1997 | Bezwada et al. |
| 5,602,010 A | 2/1997 | Hauptmann et al. |
| 5,605,688 A | 2/1997 | Himmler et al. |
| 5,607,687 A | 3/1997 | Bezwada et al. |
| 5,609,885 A | 3/1997 | Rivera et al. |
| 5,614,221 A | 3/1997 | Fjellstrom |
| 5,614,492 A | 3/1997 | Habener |
| 5,618,552 A | 4/1997 | Bezwada et al. |
| 5,620,698 A | 4/1997 | Bezwada et al. |
| 5,620,705 A | 4/1997 | Dong et al. |
| 5,633,011 A | 5/1997 | Dong et al. |
| 5,635,213 A | 6/1997 | Nystrom et al. |
| 5,639,477 A | 6/1997 | Maruyama et al. |
| 5,645,850 A | 7/1997 | Bezwada et al. |
| 5,648,088 A | 7/1997 | Bezwada et al. |
| 5,660,847 A | 8/1997 | Magruder et al. |
| 5,660,858 A | 8/1997 | Parikh et al. |
| 5,660,861 A | 8/1997 | Jao et al. |
| 5,668,170 A | 9/1997 | Gyory |
| 5,676,942 A | 10/1997 | Testa et al. |
| 5,686,097 A | 11/1997 | Taskovich et al. |
| 5,690,925 A | 11/1997 | Gray et al. |
| 5,690,952 A | 11/1997 | Magruder et al. |
| 5,698,213 A | 12/1997 | Jamiolkowski et al. |
| 5,700,486 A | 12/1997 | Canal et al. |
| 5,700,583 A | 12/1997 | Jamiolkowski et al. |
| 5,703,200 A | 12/1997 | Bezwada et al. |
| 5,711,967 A | 1/1998 | Juch |
| 5,713,847 A | 2/1998 | Howard, III et al. |
| 5,728,088 A | 3/1998 | Magruder et al. |
| 5,728,396 A | 3/1998 | Peery et al. |
| 5,733,572 A | 3/1998 | Unger et al. |
| 5,736,159 A | 4/1998 | Chen et al. |
| 5,738,845 A | 4/1998 | Imakawa |
| 5,747,058 A | 5/1998 | Tipton et al. |
| 5,756,450 A | 5/1998 | Hahn et al. |
| 5,782,396 A | 7/1998 | Mastri et al. |
| 5,795,591 A | 8/1998 | Lee et al. |
| 5,795,779 A | 8/1998 | McCormick et al. |
| 5,807,876 A | 9/1998 | Armistead et al. |
| 5,814,323 A | 9/1998 | Lyle |
| 5,817,129 A | 10/1998 | Labrecque et al. |
| 5,830,501 A | 11/1998 | Dong et al. |
| 5,836,935 A | 11/1998 | Ashton et al. |
| 5,843,891 A | 12/1998 | Sherman |
| 5,844,017 A | 12/1998 | Jamiolkowski et al. |
| 5,858,746 A | 1/1999 | Hubbell et al. |
| 5,859,150 A | 1/1999 | Jamiolkowski et al. |
| 5,861,166 A | 1/1999 | Eckenhoff |
| 5,871,770 A | 2/1999 | Magruder et al. |
| 5,874,388 A | 2/1999 | Hsu |
| 5,876,746 A | 3/1999 | Jona et al. |
| 5,882,676 A | 3/1999 | Lee et al. |
| 5,904,935 A | 5/1999 | Eckenhoff et al. |
| 5,906,816 A | 5/1999 | Soos et al. |
| 5,906,830 A | 5/1999 | Farinas et al. |
| 5,908,621 A | 6/1999 | Glue et al. |
| 5,928,666 A | 7/1999 | Farinas et al. |
| 5,932,547 A | 8/1999 | Stevenson et al. |
| 5,938,654 A | 8/1999 | Wong et al. |
| 5,939,286 A | 8/1999 | Johnson et al. |
| 5,942,223 A | 8/1999 | Bazer et al. |
| 5,948,430 A | 9/1999 | Zerbe et al. |
| 5,958,909 A | 9/1999 | Habener |
| 5,962,023 A | 10/1999 | Jamiolkowski et al. |
| 5,972,370 A | 10/1999 | Eckenhoff et al. |
| 5,972,373 A | 10/1999 | Yajima et al. |
| 5,976,109 A | 11/1999 | Heruth |
| 5,985,305 A | 11/1999 | Peery et al. |
| 5,997,527 A | 12/1999 | Gumucio et al. |
| 5,997,902 A | 12/1999 | Maruyama et al. |
| 6,007,805 A | 12/1999 | Foster et al. |
| 6,017,545 A | 1/2000 | Modi |
| 6,022,561 A | 2/2000 | Carlsson et al. |
| 6,029,361 A | 2/2000 | Newman |
| 6,060,450 A | 5/2000 | Soos et al. |
| 6,069,133 A | 5/2000 | Carlo et al. |
| 6,074,660 A | 6/2000 | Jamiolkowski et al. |
| 6,074,673 A | 6/2000 | Guillen |
| 6,100,346 A | 8/2000 | Jamiolkowski et al. |
| 6,113,938 A | 9/2000 | Chen et al. |
| 6,124,261 A | 9/2000 | Stevenson et al. |
| 6,124,281 A | 9/2000 | Lewis et al. |
| 6,127,520 A | 10/2000 | Ueda et al. |
| 6,129,761 A | 10/2000 | Hubbell |
| 6,130,200 A | 10/2000 | Brodbeck et al. |
| 6,132,420 A | 10/2000 | Dionne et al. |
| 6,133,249 A | 10/2000 | Hills |
| 6,133,429 A | 10/2000 | Davis et al. |
| 6,147,168 A | 11/2000 | Jamiolkowski et al. |
| 6,156,331 A | 12/2000 | Peery et al. |
| 6,172,046 B1 | 1/2001 | Albrecht |
| 6,174,547 B1 | 1/2001 | Dong et al. |
| 6,177,096 B1 | 1/2001 | Zerbe et al. |
| 6,183,461 B1 | 2/2001 | Matsuura et al. |
| 6,187,095 B1 | 2/2001 | Labrecque et al. |
| 6,190,350 B1 | 2/2001 | Davis et al. |
| 6,191,102 B1 | 2/2001 | DiMarchi et al. |
| 6,204,022 B1 | 3/2001 | Johnson et al. |
| 6,217,906 B1 | 4/2001 | Gumucio et al. |
| 6,217,908 B1 | 4/2001 | Mathiowitz et al. |
| 6,218,431 B1 | 4/2001 | Schoen et al. |
| 6,224,894 B1 | 5/2001 | Jamiolkowski et al. |
| 6,235,712 B1 | 5/2001 | Stevenson et al. |
| 6,245,357 B1 | 6/2001 | Edgren et al. |
| 6,248,112 B1 | 6/2001 | Gambale et al. |
| 6,251,435 B1 | 6/2001 | Jamiolkowski et al. |
| 6,258,377 B1 | 7/2001 | New et al. |
| 6,261,584 B1 | 7/2001 | Peery et al. |
| 6,268,343 B1 | 7/2001 | Knudsen et al. |
| 6,270,787 B1 | 8/2001 | Ayer |
| 6,283,949 B1 | 9/2001 | Roorda |
| 6,284,264 B1 | 9/2001 | Zerbe et al. |
| 6,284,725 B1 | 9/2001 | Coolidge et al. |
| 6,284,727 B1 | 9/2001 | Kim et al. |
| 6,287,295 B1 | 9/2001 | Chen et al. |
| 6,329,336 B1 | 12/2001 | Bridon et al. |

(56) References Cited

U.S. PATENT DOCUMENTS

| | | |
|---|---|---|
| 6,331,311 B1 | 12/2001 | Brodbeck et al. |
| 6,372,218 B1 | 4/2002 | Cummins, Jr. |
| 6,372,256 B2 | 4/2002 | Jamiolkowski et al. |
| 6,375,978 B1 | 4/2002 | Kleiner et al. |
| 6,395,292 B2 | 5/2002 | Peery et al. |
| 6,403,655 B1 | 6/2002 | Bezwada et al. |
| 6,419,952 B2 | 7/2002 | Wong et al. |
| 6,433,144 B1 | 8/2002 | Morris et al. |
| 6,436,091 B1 | 8/2002 | Harper et al. |
| 6,447,522 B2 | 9/2002 | Gambale et al. |
| 6,451,974 B1 | 9/2002 | Hansen |
| 6,458,385 B2 | 10/2002 | Jamiolkowski et al. |
| 6,458,924 B2 | 10/2002 | Knudsen et al. |
| 6,464,688 B1 | 10/2002 | Harper et al. |
| 6,468,961 B1 | 10/2002 | Brodbeck et al. |
| 6,471,688 B1 | 10/2002 | Harper et al. |
| 6,472,512 B1 | 10/2002 | LaFleur et al. |
| 6,485,706 B1 | 11/2002 | McCoy et al. |
| 6,506,724 B1 | 1/2003 | Hiles et al. |
| 6,508,808 B1 | 1/2003 | Carr et al. |
| 6,514,500 B1 | 2/2003 | Bridon et al. |
| 6,514,517 B2 | 2/2003 | Jamiolkowski et al. |
| 6,524,305 B1 | 2/2003 | Peterson et al. |
| 6,528,486 B1 | 3/2003 | Larsen et al. |
| 6,541,021 B1 | 4/2003 | Johnson et al. |
| 6,544,252 B1 | 4/2003 | Theeuwes et al. |
| 6,551,613 B1 | 4/2003 | Dong et al. |
| 6,569,420 B2 | 5/2003 | Chen et al. |
| 6,572,890 B2 | 6/2003 | Faour et al. |
| 6,579,851 B2 | 6/2003 | Goeke et al. |
| 6,592,887 B2 | 7/2003 | Zerbe et al. |
| 6,593,295 B2 | 7/2003 | Bridon et al. |
| 6,635,268 B2 | 10/2003 | Peery et al. |
| 6,670,368 B1 | 12/2003 | Breault et al. |
| 6,673,767 B1 | 1/2004 | Brodbeck et al. |
| 6,682,522 B2 | 1/2004 | Carr et al. |
| 6,703,225 B1 | 3/2004 | Kojima et al. |
| 6,703,359 B1 | 3/2004 | Young et al. |
| 6,706,689 B2 | 3/2004 | Coolidge et al. |
| 6,709,671 B2 | 3/2004 | Zerbe et al. |
| 6,720,407 B1 | 4/2004 | Hughes et al. |
| 6,730,328 B2 | 5/2004 | Maskiewicz et al. |
| 6,767,887 B1 | 7/2004 | Hoffmann et al. |
| 6,821,949 B2 | 11/2004 | Bridon et al. |
| 6,833,256 B1 | 12/2004 | Pontzer et al. |
| 6,835,194 B2 | 12/2004 | Johnson et al. |
| 6,840,931 B2 | 1/2005 | Peterson et al. |
| 6,849,708 B1 | 2/2005 | Habener |
| 6,849,714 B1 | 2/2005 | Bridon et al. |
| 6,858,576 B1 | 2/2005 | Young et al. |
| 6,872,700 B1 | 3/2005 | Young et al. |
| 6,875,748 B2 | 4/2005 | Manthorpe et al. |
| 6,887,470 B1 | 5/2005 | Bridon et al. |
| 6,887,849 B2 | 5/2005 | Bridon et al. |
| 6,899,887 B2 | 5/2005 | Ayer |
| 6,902,744 B1 | 6/2005 | Kolterman et al. |
| 6,903,186 B1 | 6/2005 | Dong |
| 6,923,800 B2 | 8/2005 | Chen et al. |
| 6,924,264 B1 | 8/2005 | Prickett et al. |
| 6,939,556 B2 | 9/2005 | Lautenbach |
| 6,956,026 B2 | 10/2005 | Beeley et al. |
| 6,969,702 B2 | 11/2005 | Bertilsson et al. |
| 6,976,981 B2 | 12/2005 | Ayer |
| 6,989,366 B2 | 1/2006 | Beeley et al. |
| 6,992,065 B2 | 1/2006 | Okumu |
| 6,997,922 B2 | 2/2006 | Theeuwes et al. |
| 7,014,636 B2 | 3/2006 | Gilbert |
| 7,022,674 B2 | 4/2006 | DeFelippis et al. |
| 7,041,646 B2 | 5/2006 | Pan et al. |
| 7,074,423 B2 | 7/2006 | Fereira et al. |
| 7,084,243 B2 | 8/2006 | Glaesner et al. |
| 7,101,567 B1 | 9/2006 | Sano et al. |
| 7,101,843 B2 | 9/2006 | Glaesner et al. |
| 7,112,335 B2 | 9/2006 | Lautenbach |
| 7,115,569 B2 | 10/2006 | Beeley et al. |
| 7,138,375 B2 | 11/2006 | Beeley et al. |
| 7,138,486 B2 | 11/2006 | Habener et al. |
| 7,141,547 B2 | 11/2006 | Rosen et al. |
| 7,144,863 B2 | 12/2006 | DeFelippis et al. |
| 7,153,825 B2 | 12/2006 | Young et al. |
| 7,157,555 B1 | 1/2007 | Beeley et al. |
| 7,163,688 B2 | 1/2007 | Peery et al. |
| 7,199,217 B2 | 4/2007 | DiMarchi et al. |
| 7,205,409 B2 | 4/2007 | Pei et al. |
| 7,207,982 B2 | 4/2007 | Dionne et al. |
| 7,241,457 B2 | 7/2007 | Chen et al. |
| 7,258,869 B1 | 8/2007 | Berry et al. |
| 7,297,761 B2 | 11/2007 | Beeley et al. |
| 7,316,680 B2 | 1/2008 | Gilbert |
| 7,393,827 B2 | 7/2008 | Nadler |
| 7,407,499 B2 | 8/2008 | Trautman |
| 7,442,682 B2 | 10/2008 | Kitaura et al. |
| 7,456,254 B2 | 11/2008 | Wright et al. |
| 7,459,432 B2 | 12/2008 | Cowley et al. |
| 7,521,423 B2 | 4/2009 | Young et al. |
| 7,563,871 B2 | 7/2009 | Wright et al. |
| 7,612,176 B2 | 11/2009 | Wright et al. |
| 7,655,254 B2 | 2/2010 | Dennis et al. |
| 7,655,257 B2 | 2/2010 | Peery et al. |
| 7,666,835 B2 | 2/2010 | Bloom et al. |
| 7,682,356 B2 * | 3/2010 | Alessi ................ A61K 9/0004 604/222 |
| 7,727,519 B2 | 6/2010 | Moran |
| 7,731,947 B2 | 6/2010 | Eliaz et al. |
| 7,741,269 B2 | 6/2010 | Young et al. |
| 7,825,091 B2 | 11/2010 | Bloom et al. |
| 7,829,109 B2 | 11/2010 | Chen et al. |
| 7,833,543 B2 | 11/2010 | Gibson et al. |
| 7,879,028 B2 * | 2/2011 | Alessi ................ A61K 9/0004 604/222 |
| 7,919,109 B2 | 4/2011 | Berry et al. |
| 7,959,938 B2 | 6/2011 | Rohloff et al. |
| 7,964,183 B2 | 6/2011 | Eliaz et al. |
| 8,048,438 B2 | 11/2011 | Berry et al. |
| 8,052,996 B2 * | 11/2011 | Lautenbach ......... A61K 9/0004 424/423 |
| 8,058,233 B2 | 11/2011 | Cowley et al. |
| 8,101,576 B2 | 1/2012 | Bloom |
| 8,114,430 B2 | 2/2012 | Rohloff et al. |
| 8,114,437 B2 * | 2/2012 | Rohloff ................ A61K 9/0004 424/423 |
| 8,158,150 B2 * | 4/2012 | Lautenbach ......... A61K 9/0004 424/423 |
| 8,173,150 B2 | 5/2012 | Berry et al. |
| 8,206,745 B2 * | 6/2012 | Rohloff ................ A61K 9/0004 424/486 |
| 8,211,467 B2 * | 7/2012 | Rohloff ................ A61K 9/0004 424/423 |
| 8,217,001 B2 | 7/2012 | Cowley et al. |
| 8,257,691 B2 | 9/2012 | Eliaz et al. |
| 8,263,545 B2 | 9/2012 | Levy et al. |
| 8,263,736 B2 | 9/2012 | Bloom |
| 8,268,341 B2 | 9/2012 | Berry |
| 8,273,365 B2 * | 9/2012 | Lautenbach ......... A61K 9/0004 424/423 |
| 8,273,713 B2 | 9/2012 | Pittner et al. |
| 8,278,267 B2 | 10/2012 | Weyer et al. |
| 8,298,561 B2 | 10/2012 | Alessi et al. |
| 8,299,025 B2 | 10/2012 | Alessi et al. |
| 8,343,140 B2 * | 1/2013 | Alessi ................ A61K 9/0004 604/892.1 |
| 8,367,095 B2 * | 2/2013 | Lautenbach ......... A61K 9/0004 424/423 |
| 8,372,424 B2 | 2/2013 | Berry et al. |
| 8,398,967 B2 | 3/2013 | Eliaz et al. |
| 8,440,226 B2 | 5/2013 | Rohloff et al. |
| 8,460,694 B2 | 6/2013 | Rohloff et al. |
| 8,470,353 B2 * | 6/2013 | Lautenbach ......... A61K 9/0004 424/422 |
| 8,801,700 B2 * | 8/2014 | Alessi ................ A61K 9/0004 604/222 |
| 8,865,202 B2 | 10/2014 | Zerbe et al. |

(56) References Cited

U.S. PATENT DOCUMENTS

| | | | |
|---|---|---|---|
| 8,926,595 B2* | 1/2015 | Alessi | A61K 9/0004 604/892.1 |
| 8,940,316 B2 | 1/2015 | Alessi et al. | |
| 8,992,961 B2 | 3/2015 | Berry et al. | |
| 8,992,962 B2* | 3/2015 | Lautenbach | A61K 9/0004 424/422 |
| 9,095,553 B2 | 8/2015 | Rohloff et al. | |
| 2001/0012511 A1 | 8/2001 | Bezwada et al. | |
| 2001/0021377 A1 | 9/2001 | Jamiolkowski et al. | |
| 2001/0021822 A1 | 9/2001 | Ayer | |
| 2001/0022974 A1 | 9/2001 | Ayer | |
| 2001/0027311 A1 | 10/2001 | Chen et al. | |
| 2001/0036472 A1 | 11/2001 | Wong et al. | |
| 2001/0037190 A1 | 11/2001 | Jung | |
| 2002/0001631 A1 | 1/2002 | Okumu | |
| 2002/0004481 A1 | 1/2002 | Cleland et al. | |
| 2002/0012818 A1 | 1/2002 | Ruppi et al. | |
| 2002/0034532 A1 | 3/2002 | Brodbeck et al. | |
| 2002/0037309 A1 | 3/2002 | Jaworowicz et al. | |
| 2002/0048600 A1 | 4/2002 | Bhatt et al. | |
| 2002/0136848 A1 | 9/2002 | Yoshii et al. | |
| 2002/0137666 A1 | 9/2002 | Beeley et al. | |
| 2002/0141985 A1 | 10/2002 | Pittner et al. | |
| 2002/0197185 A1 | 12/2002 | Jamiolkowski et al. | |
| 2003/0032947 A1 | 2/2003 | Harper et al. | |
| 2003/0044467 A1 | 3/2003 | Brodbeck et al. | |
| 2003/0045454 A1 | 3/2003 | Okumu et al. | |
| 2003/0059376 A1 | 3/2003 | Libbey, III et al. | |
| 2003/0060425 A1 | 3/2003 | Ahlem et al. | |
| 2003/0104063 A1 | 6/2003 | Babcock et al. | |
| 2003/0108608 A1 | 6/2003 | Laridon et al. | |
| 2003/0108609 A1 | 6/2003 | Berry et al. | |
| 2003/0113380 A1 | 6/2003 | Ramstack et al. | |
| 2003/0118660 A1 | 6/2003 | Rickey et al. | |
| 2003/0138403 A1 | 7/2003 | Drustrup | |
| 2003/0138491 A1 | 7/2003 | Tracy et al. | |
| 2003/0157178 A1 | 8/2003 | Chen et al. | |
| 2003/0170289 A1 | 9/2003 | Chen et al. | |
| 2003/0180364 A1 | 9/2003 | Chen et al. | |
| 2003/0186858 A1 | 10/2003 | Arentsen | |
| 2003/0211974 A1 | 11/2003 | Brodbeck et al. | |
| 2003/0215515 A1 | 11/2003 | Truong-Le et al. | |
| 2004/0001689 A1 | 1/2004 | Goldsmith et al. | |
| 2004/0001889 A1 | 1/2004 | Chen et al. | |
| 2004/0002442 A1 | 1/2004 | Pan et al. | |
| 2004/0022859 A1 | 2/2004 | Chen et al. | |
| 2004/0024068 A1 | 2/2004 | Levy et al. | |
| 2004/0024069 A1 | 2/2004 | Chen et al. | |
| 2004/0029784 A1 | 2/2004 | Hathaway | |
| 2004/0039376 A1 | 2/2004 | Peery et al. | |
| 2004/0097906 A1 | 5/2004 | Fereira et al. | |
| 2004/0101557 A1 | 5/2004 | Gibson et al. | |
| 2004/0102762 A1 | 5/2004 | Gilbert | |
| 2004/0115236 A1 | 6/2004 | Chan et al. | |
| 2004/0142867 A1 | 7/2004 | Oi et al. | |
| 2004/0151753 A1 | 8/2004 | Chen et al. | |
| 2004/0157951 A1 | 8/2004 | Wolf | |
| 2004/0198654 A1 | 10/2004 | Glaesner et al. | |
| 2004/0209801 A1 | 10/2004 | Brand et al. | |
| 2004/0224903 A1 | 11/2004 | Berry et al. | |
| 2004/0225113 A1 | 11/2004 | LaFleur et al. | |
| 2004/0243106 A1 | 12/2004 | Ayer | |
| 2004/0265273 A1 | 12/2004 | Li et al. | |
| 2004/0266683 A1 | 12/2004 | Hathaway et al. | |
| 2004/0266692 A1 | 12/2004 | Young et al. | |
| 2005/0004557 A1 | 1/2005 | Russell | |
| 2005/0008661 A1 | 1/2005 | Fereira et al. | |
| 2005/0009742 A1 | 1/2005 | Bertilsson et al. | |
| 2005/0010196 A1 | 1/2005 | Fereira et al. | |
| 2005/0070883 A1 | 3/2005 | Brown et al. | |
| 2005/0079200 A1 | 4/2005 | Rathenow et al. | |
| 2005/0079202 A1 | 4/2005 | Chen et al. | |
| 2005/0095284 A1 | 5/2005 | Trautman | |
| 2005/0101943 A1 | 5/2005 | Ayer et al. | |
| 2005/0106214 A1 | 5/2005 | Chen | |
| 2005/0112188 A1 | 5/2005 | Eliaz et al. |
| 2005/0118206 A1 | 6/2005 | Luk et al. |
| 2005/0118221 A1 | 6/2005 | Blakely et al. |
| 2005/0131386 A1 | 6/2005 | Freeman et al. |
| 2005/0175701 A1 | 8/2005 | Pan et al. |
| 2005/0201980 A1 | 9/2005 | Moran |
| 2005/0215475 A1 | 9/2005 | Ong et al. |
| 2005/0266087 A1 | 12/2005 | Junnarkar et al. |
| 2005/0271702 A1 | 12/2005 | Wright et al. |
| 2005/0276856 A1 | 12/2005 | Fereira et al. |
| 2005/0281879 A1 | 12/2005 | Chen et al. |
| 2006/0013879 A9 | 1/2006 | Brodbeck et al. |
| 2006/0014678 A1 | 1/2006 | Cowley et al. |
| 2006/0030526 A1 | 2/2006 | Liu et al. |
| 2006/0069029 A1 | 3/2006 | Kolterman et al. |
| 2006/0084604 A1 | 4/2006 | Kitaura et al. |
| 2006/0094652 A1 | 5/2006 | Levy et al. |
| 2006/0141040 A1 | 6/2006 | Chen et al. |
| 2006/0142234 A1 | 6/2006 | Chen et al. |
| 2006/0160736 A1 | 7/2006 | Nadler |
| 2006/0178304 A1 | 8/2006 | Juul-Mortensen et al. |
| 2006/0193918 A1 | 8/2006 | Rohloff et al. |
| 2006/0216242 A1 | 9/2006 | Rohloff et al. |
| 2006/0233841 A1 | 10/2006 | Brodbeck et al. |
| 2006/0246138 A1 | 11/2006 | Rohloff et al. |
| 2006/0251618 A1 | 11/2006 | Dennis et al. |
| 2006/0263433 A1 | 11/2006 | Ayer et al. |
| 2006/0264890 A1 | 11/2006 | Moberg et al. |
| 2006/0280795 A1 | 12/2006 | Penhasi et al. |
| 2006/0293232 A1 | 12/2006 | Levy et al. |
| 2007/0027105 A1 | 2/2007 | Junnarkar et al. |
| 2007/0166352 A1 | 7/2007 | Wright et al. |
| 2007/0248572 A1 | 10/2007 | Moran et al. |
| 2007/0281024 A1 | 12/2007 | Lautenbach et al. |
| 2008/0038316 A1 | 2/2008 | Wong et al. |
| 2008/0064636 A1 | 3/2008 | Bloom et al. |
| 2008/0091176 A1 | 4/2008 | Alessi et al. |
| 2008/0112994 A1 | 5/2008 | Junnarkar et al. |
| 2008/0200383 A1 | 8/2008 | Jennings et al. |
| 2008/0207512 A1 | 8/2008 | Roth et al. |
| 2008/0226625 A1 | 9/2008 | Berry et al. |
| 2008/0226689 A1 | 9/2008 | Berry et al. |
| 2008/0260838 A1 | 10/2008 | Hokenson et al. |
| 2008/0260840 A1 | 10/2008 | Alessi et al. |
| 2008/0312157 A1 | 12/2008 | Levy et al. |
| 2009/0022727 A1 | 1/2009 | Houston et al. |
| 2009/0042781 A1 | 2/2009 | Petersen et al. |
| 2009/0074734 A1 | 3/2009 | Rottiers |
| 2009/0087408 A1 | 4/2009 | Berry et al. |
| 2009/0156474 A1 | 6/2009 | Roth et al. |
| 2009/0163447 A1 | 6/2009 | Maggio |
| 2009/0186817 A1 | 7/2009 | Ghosh et al. |
| 2009/0202481 A1 | 8/2009 | Li et al. |
| 2009/0202608 A1 | 8/2009 | Alessi et al. |
| 2009/0209460 A1 | 8/2009 | Young et al. |
| 2009/0210019 A1 | 8/2009 | Kim et al. |
| 2009/0215694 A1 | 8/2009 | Kolterman et al. |
| 2009/0247463 A1 | 10/2009 | Wright et al. |
| 2009/0286723 A1 | 11/2009 | Levy et al. |
| 2009/0312246 A1 | 12/2009 | Baron et al. |
| 2010/0092566 A1 | 4/2010 | Alessi et al. |
| 2010/0105627 A1 | 4/2010 | Salama et al. |
| 2010/0144621 A1 | 6/2010 | Kim et al. |
| 2010/0185184 A1 | 7/2010 | Alessi et al. |
| 2010/0297209 A1 | 11/2010 | Rohloff et al. |
| 2011/0076317 A1 | 3/2011 | Alessi et al. |
| 2011/0104111 A1 | 5/2011 | Rohloff et al. |
| 2011/0152182 A1 | 6/2011 | Alsina-Fernandez et al. |
| 2011/0160708 A1 | 6/2011 | Berry et al. |
| 2011/0166554 A1 | 7/2011 | Alessi et al. |
| 2011/0264077 A1 | 10/2011 | Rohloff et al. |
| 2011/0306549 A1 | 12/2011 | Tatarkiewicz et al. |
| 2012/0178687 A1 | 7/2012 | Alessi et al. |
| 2012/0208755 A1 | 8/2012 | Leung |
| 2013/0052237 A1 | 2/2013 | Eliaz et al. |
| 2015/0111818 A1 | 4/2015 | Alessi et al. |
| 2015/0231256 A1 | 8/2015 | Berry et al. |

(56) References Cited

U.S. PATENT DOCUMENTS

FOREIGN PATENT DOCUMENTS

| | | |
|---|---|---|
| EP | 0295411 | 12/1988 |
| EP | 0368339 | 5/1990 |
| EP | 0373867 | 6/1990 |
| EP | 0431942 | 6/1991 |
| EP | 0379147 | 9/1994 |
| EP | 0627231 | 12/1994 |
| EP | 0729747 | 5/1997 |
| EP | 0771817 | 5/1997 |
| EP | 0841359 | 5/1998 |
| EP | 0767689 | 6/1999 |
| EP | 1046399 | 10/2000 |
| EP | 1084703 | 3/2001 |
| EP | 1600187 | 1/2009 |
| EP | 2020990 | 9/2010 |
| FR | 640907 | 7/1928 |
| GB | 1049104 | 11/1966 |
| GB | 1518683 | 7/1978 |
| JP | 9241153 | 9/1997 |
| JP | 11-100353 | 4/1999 |
| JP | 2006/213727 A | 8/2006 |
| NZ | 592113 | 8/2012 |
| TW | 200634060 | 10/2006 |
| WO | WO 91/07160 | 5/1991 |
| WO | WO 93/06819 | 4/1993 |
| WO | WO 93/06821 | 4/1993 |
| WO | WO 93/08832 | 5/1993 |
| WO | WO 93/09763 | 5/1993 |
| WO | WO 93/23083 | 11/1993 |
| WO | WO 94/09743 | 5/1994 |
| WO | WO 94/21262 | 9/1994 |
| WO | WO 95/01167 | 1/1995 |
| WO | WO 95/09006 | 4/1995 |
| WO | WO 95/09007 | 4/1995 |
| WO | WO 95/34285 | 12/1995 |
| WO | WO 96001134 | 1/1996 |
| WO | WO 96/03116 | 2/1996 |
| WO | WO 96/39142 | 12/1996 |
| WO | WO 96/40049 | 12/1996 |
| WO | WO 96/40139 | 12/1996 |
| WO | WO 96/40355 | 12/1996 |
| WO | WO 97/15289 | 5/1997 |
| WO | WO 97/15296 | 5/1997 |
| WO | WO 97/28181 | 8/1997 |
| WO | WO 97/46204 | 12/1997 |
| WO | WO 97/47339 | 12/1997 |
| WO | WO 98/00152 | 1/1998 |
| WO | WO 98/00157 | 1/1998 |
| WO | WO 98/00158 | 1/1998 |
| WO | WO 98/02169 | 1/1998 |
| WO | WO 98/16250 | 4/1998 |
| WO | WO 98/17315 | 4/1998 |
| WO | WO 98/20930 | 5/1998 |
| WO | WO 98/27960 | 7/1998 |
| WO | WO 98/27962 | 7/1998 |
| WO | WO 98/27963 | 7/1998 |
| WO | WO 98/30231 | 7/1998 |
| WO | WO 98/32463 | 7/1998 |
| WO | WO 98/42317 | 10/1998 |
| WO | WO 98/47487 | 10/1998 |
| WO | WO 98/51282 | 11/1998 |
| WO | WO 99/03453 | 1/1999 |
| WO | WO 99/04767 | 2/1999 |
| WO | WO 99/04768 | 2/1999 |
| WO | WO 99/16419 | 4/1999 |
| WO | WO 99/25728 | 5/1999 |
| WO | WO 99/29306 | 6/1999 |
| WO | WO 99/33446 | 7/1999 |
| WO | WO 99/33449 | 7/1999 |
| WO | WO 99/39700 | 8/1999 |
| WO | WO 99/40788 | 8/1999 |
| WO | WO 99/44659 | 9/1999 |
| WO | WO 99/62501 | 12/1999 |
| WO | WO 99/64061 | 12/1999 |
| WO | WO 00/13663 | 3/2000 |
| WO | WO 00/29206 | 5/2000 |
| WO | WO 00/38652 | 7/2000 |
| WO | WO 00/39280 | 7/2000 |
| WO | WO 00/40273 | 7/2000 |
| WO | WO 00/41548 | 7/2000 |
| WO | WO 00/45790 | 8/2000 |
| WO | WO 00/54745 | 9/2000 |
| WO | WO 00/66138 | 11/2000 |
| WO | WO 01/43528 | 6/2001 |
| WO | WO 01/51041 | 7/2001 |
| WO | WO 01/78683 | 10/2001 |
| WO | WO 02/28366 | 4/2002 |
| WO | WO 02/36072 | 5/2002 |
| WO | WO 02/43800 | 6/2002 |
| WO | WO 02/45752 | 6/2002 |
| WO | WO 02/47716 | 6/2002 |
| WO | WO 02/067895 | 9/2002 |
| WO | WO 02/069983 | 9/2002 |
| WO | WO 02/076344 | 10/2002 |
| WO | WO 02/085428 | 10/2002 |
| WO | WO 03/000230 | 1/2003 |
| WO | WO 03/011892 | 2/2003 |
| WO | WO 03/024357 | 3/2003 |
| WO | WO 03/024503 | 3/2003 |
| WO | WO 03/030923 | 4/2003 |
| WO | WO 03/041684 | 5/2003 |
| WO | WO 03/072113 | 9/2003 |
| WO | WO 03/072133 | 9/2003 |
| WO | WO 2004/002565 | 1/2004 |
| WO | WO 2004/052336 | 6/2004 |
| WO | WO 2004/056338 | 7/2004 |
| WO | WO 2004/089335 | 10/2004 |
| WO | WO 2005/048930 | 6/2005 |
| WO | WO 2005/048952 | 6/2005 |
| WO | WO 2005/102293 | 11/2005 |
| WO | WO 2006/017772 | 2/2006 |
| WO | WO 2006/023526 | 3/2006 |
| WO | WO 2006/081279 | 8/2006 |
| WO | WO 2006/083761 | 8/2006 |
| WO | WO 2006/084139 | 8/2006 |
| WO | WO 2006/101815 | 9/2006 |
| WO | WO 2006/111169 | 10/2006 |
| WO | WO 2007/024700 | 3/2007 |
| WO | WO 2007/056681 | 5/2007 |
| WO | WO 2007/075534 | 7/2007 |
| WO | WO 2007/084460 | 7/2007 |
| WO | WO 2007/133778 | 11/2007 |
| WO | WO 2007/140416 | 12/2007 |
| WO | WO 2008/021133 | 2/2008 |
| WO | WO 2008/061355 | 5/2008 |
| WO | WO 2008/133908 | 11/2008 |
| WO | WO 2008/134425 | 11/2008 |
| WO | WO 2009/109927 | 9/2009 |

OTHER PUBLICATIONS

International Preliminary Report on Patentability for International Application No. PCT/US2004/010107, dated Feb. 24, 2005.
International Search Report and Written Opinion for International Application No. PCT/US2004/010106, mailed Aug. 30, 2004.
International Preliminary Report on Patentability for International Application No. PCT/US2004/010106, dated Jul. 8, 2005.
Office Action for U.S. Appl. No. 11/347,562, mailed Feb. 4, 2010, 9 pages.
Office Action for U.S. Appl. No. 11/347,562, mailed Sep. 7, 2010, 20 pages.
International Search Report and Written Opinion for International Application No. PCT/US2006/003192, mailed Jul. 28, 2006.
International Preliminary Report on Patentability for International Application No. PCT/US2006/003192, dated Aug. 7, 2007.
Office Action for U.S. Appl. No. 12/827,265, mailed Mar. 30, 2011, 10 pages.
Office Action for U.S. Appl. No. 13/158,137, mailed Dec. 13, 2011, 13 pages.
Office Action for U.S. Appl. No. 13/526,375, mailed Sep. 14, 2012, 13 pages.

(56) References Cited

OTHER PUBLICATIONS

Office Action for U.S. Appl. No. 12/925,864, mailed Dec. 13, 2011, 11 pages.
Office Action for U.S. Appl. No. 13/647,228, mailed Jan. 2, 2013, 5 pages.
Office Action for U.S. Appl. No. 13/647,873, mailed Sep. 11, 2014, 7 pages.
Office Action for U.S. Appl. No. 13/647,873, mailed Jan. 3, 2013, 5 pages.
Office Action for U.S. Appl. No. 13/647,873, mailed Jun. 18, 2013, 5 pages.
Office Action for U.S. Appl. No. 11/755,494, mailed Dec. 27, 2010, 10 pages.
Office Action for U.S. Appl. No. 11/755,494, mailed Jun. 8, 2011, 15 pages.
International Search Report and Written Opinion for International Application No. PCT/US2007/069990, mailed Feb. 26, 2008.
International Preliminary Report on Patentability for International Application No. PCT/US2007/069990, dated Dec. 3, 2008.
Office Action for U.S. Appl. No. 13/433,287, mailed Jun. 19, 2012, 5 pages.
Office Action for U.S. Appl. No. 13/601,939, mailed Oct. 25, 2012, 5 pages.
Office Action for U.S. Appl. No. 13/740,187, mailed Apr. 11, 2013, 6 pages.
Office Action for U.S. Appl. No. 13/898,358, mailed Jul. 17, 2014, 6 pages.
Office Action for U.S. Appl. No. 13/209,328, mailed Feb. 16, 2012, 5 pages.
International Search Report and Written Opinion for International Application No. PCT/US2004/009755, mailed Nov. 22, 2004.
International Preliminary Report on Patentability for International Application No. PCT/US2004/009755, dated Jul. 8, 2005.
Office Action for U.S. Appl. No. 12/148,896, mailed Aug. 23, 2012, 6 pages.
Office Action for U.S. Appl. No. 12/148,896, mailed Oct. 20, 2009, 10 pages.
Office Action for U.S. Appl. No. 12/148,896, mailed May 14, 2010, 8 pages.
International Preliminary Report on Patentability for International Application No. PCT/US2008/005235, mailed Apr. 11, 2008.
International Search Report and Written Opinion for International Application No. PCT/US2008/005235, mailed Dec. 19, 2008.
Office Action for U.S. Appl. No. 12/927,432, mailed Mar. 26, 2014, 8 pages.
Bell, G. I. et al., "Hamster preproglucagon contains the sequence of glucagon and two related peptides," Nature, 302:716-718 (1983).
Clark, J. B. et al., "The diabetic Zucker fatty rat," Proc. Soc. Exp. Biol., Med., 173(1): 68-75 (1983).
Henry, R. R. et al., "Comparing ITCA 650, continuous subcutaneous delivery of exenatide via DUROS® device, vs. twice daily exenatide injections in metformin-treated type 2 diabetes," ITCA 650 phase 2 oral presentation at the 46th Annual Meeting of the European Association for the Study of Diabetes in Stockholm, Sweden (Sep. 20-24, 2010).
Dash, A. K. et al., "Therapeutic applications of implantable drug delivery systems," Journal of Pharmacological and Toxicological Methods, 40(1):1-12 (1998).
Deacon, C. F. et al., "GLP-1-(9-36) amide reduces blood glucose in anesthetized pigs by a mechanism that does not involve insulin secretion," Am. J. Physiol. Endocrinol. Metab., 282:E873-E879 (2002).
Efendic, S. et al., et al., "Overview of incretin hormones," Horm. Metab. Res., 36(11-12):742-746 (2004).
Eissele, R. et al., "Rat gastric somatostatin and gastrin release: interactions of exendin-4 and truncated glucagon-like peptide-1 (GLP-1) amide," Life Sci., 55(8):629-634 (1994).
Eng, J. et al., "Purification and structure of exendin-3, a new pancreatic secretagogue isolated from Heloderma horridum venom," J. Biol. Chem., 265(33):20259-20262 (1990).
Eng, J. et al., "Isolation and characterization of exendin-4, an exendin-3 analogue, from Heloderma suspectum venom. Further evidence for an exendin receptor on dispersed acini from guinea pig pancreas," J. Biol. Chem., 267(11):7402-7405 (1992).
Ghiglione, M., et al., "How glucagon-like is glucagon-like peptide-1?" Diabetologia, 27:599-600 (1984).
Goke, R. et al., "Exendin-4 is a high potency agonist and truncated exendin-(9-39)-amide an antagonist at the glucagon-like peptide 1-(7-36)-amide receptor of insulin-secreting beta-cells," J. Biol. Chem., 268(26):19650-19655 (1993).
Gutniak, M. et al., "Antidiabetogenic effect of glucagon-like peptide-1 (7-36)amide in normal subjects and patients with diabetes mellitus," N. Engl. J. Med., 326(20):1316-1322 (1992).
Heinrich, G. et al., "Pre-proglucagon messenger ribonucleic acid: nucleotide and encoded amino acid sequences of the rat pancreatic complementary deoxyribonucleic acid," Endocrinol., 115:2176-2181 (1984).
Lopez, L. C. et al., "Mammalian pancreatic preproglucagon contains three glucagon-related peptides," Proc. Natl. Acad. Sci. USA, 80(18):5485-5489 (1983).
Lund, P. K. et al., "Pancreatic preproglucagon cDNA contains two glucagon-related coding sequences arranged in tandem," Proc. Natl. Acad. Sci. USA, 79(2):345-349 (1982).
Meier, J. J. et al., "The glucagon-like peptide-1 metabolite GLP-1-(9-36) amide reduces postprandial glycemia independently of gastric emptying and insulin secretion in humans," Am. J. Physiol. Endocrinol. Metab., 290(6):E1118-E1123 (2006).
Mojsov, S., "Structural requirements for biological activity of glucagon-like peptide-I," Int. J. Peptide Protein Research, 40:333-343 (1992).
Nauck, M. A. et al., "Normalization of fasting glycaemia by intravenous GLP-1 ([7-36 amide] or [7-37]) in type 2 diabetic patients," Diabet. Med., 15(11):937-945(1998).
Patzelt, C. et al., "Identification and processing of proglucagon in pancreatic islets," Nature, 282:260-266 (1979).
Peterson, R. G. et al., "Zucker Diabetic Fatty Rat as a Model for Non-insulin-dependent Diabetes Mellitus," ILAR Journal, 32(3):16-19 (1990).
Peterson, R. G. et al., "Neuropathic complications in the Zucker diabetic fatty rat (ZDF/Drt-fa)," Frontiers in diabetes research. Lessons from Animal Diabetes III, Shafrir, E. (ed.), pp. 456-458, Smith-Gordon, London (1990).
Pohl, M. et al., "Molecular cloning of the helodermin and exendin-4 cDNAs in the lizard. Relationship to vasoactive intestinal polypeptide/pituitary adenylate cyclase activating polypeptide and glucagon-like peptide 1 and evidence against the existence of mammalian homologues," J. Biol. Chem., 273(16):9778-9784 (1998).
Press Release, Intarcia Therapeutics, Inc., "Intarcia Presents Positive ITCA 650 Phase 2 Study Results for Type 2 Diabetes at EASD," (Sep. 22, 2010).
Press Release, "Intarcia Therapeutics Announces Final Results from a Phase 2 Study of Injectable Omega Interferon plus Ribavirin for the Treatment of Hepatits C Genotype-1 ," NLV Partners Press Coverage Portofolio News (Apr. 12, 2007).
Schepp, W. et al., "Exendin-4 and exendin-(9-39)NH2: agonist and antagonist, respectively, at the rat parietal cell receptor for glucagon-like peptide-1-(7-36)NH2," Eur. J. Pharmacol., 269(2):183-191 (1994).
Sparks, J. D. et al., "Lipoprotein alterations in 10- and 20-week-old Zucker diabetic fatty rats: hyperinsulinemic versus insulinopenic hyperglycemia," Metabolism, 47(11):1315-1324 (1998).
Tseng, C. C. et al., "Glucose-dependent insulinotropic peptide: structure of the precursor and tissue-specific expression in rat," PNAS USA, 90(5):1992-1996 (1993).
Vrabec, J. T., "Tympanic membrane perforations in the diabetic rat: a model of impaired wound healing," Otolaryngol. Head Neck Surg., 118(3 Pt. 1):304-308 (1998).
Young, A. A. et al., "Glucose-lowering and insulin-sensitizing actions of exendin-4: studies in obese diabetic (ob/ob, db/db) mice, diabetic fatty Zucker rats, and diabetic rhesus monkeys (Macaca mulatta)," Diabetes, 48(5):1026-1034 (1999).

(56) References Cited

OTHER PUBLICATIONS

Office Action for U.S. Appl. No. 14/605,348, mailed Dec. 4, 2015, 14 pages.
Office Action for U.S. Appl. No. 14/749,178, mailed Feb. 11, 2016, 9 pages.
First Office Action for Chinese Patent Application No. 201410262400.X, mailed Dec. 14, 2015, 14 pages.
"Abstracts 2007," Diabetologia Clinical & Experimental Diabetes & Metabolism 50(1):S243, ¶ [0586] (Aug. 21, 2007) (XP002538652).
Jetschmann et al., "Open-label rising-dose study of omega interferon in IFN-naive patients with chronic hepatitis C," Gastroenterology 122:A278-A347 (Apr. 1, 2002) (Abstract M1454).
Bray, "Gut Signals and Energy Balance: Ghrelin, Peptide YY, Leptin, and Amylin," (slides and transcript for presentation at Medscape CME on Dec. 19, 2007).
"Implantable infusion pumps: technology poised for takeoff," BBI Newsletter 17(12):209-211 (Dec. 1994).
Adamson et al., "Phase I trial and pharmacokinetic study of all-trans-retinoic acid administered on an intermittent schedule in combination with interferon-alpha2a in pediatric patients with refractory cancer," J. Clin. Oncol. 15(11):3330-3337 (Nov. 1997).
Adolf et al., "Monoclonal antibodies and enzyme immunoassays specific for human interferon (IFN) ω1: evidence that IFN-ω1 is a component of human leukocyte IFN," Virology 175(2):410-471 (Apr. 1990).
Adolf et al., "Antigenic structure of human interferon ω1 (Interferon αII1): comparison with other human interferons," J. Gen. Virol. 68(6):1669-1676 (Jun. 1987).
Adolf et al., "Purification and characterization of natural human interferon ω1," J. Bio. Chem. 265(16):9290-9295 (Jun. 1990).
Adolf et al., "Human interferon ω1: isolation of the gene, expression in Chinese hamster ovary cells and characterization of the recombinant protein," Biochim. Biophys. Acta 108(9):167-174 (Jun. 1991).
Andrx Pharmaceuticals, LLC, ANDA for Concerta® Extended-Release Tablets, 6 pages (correspondence dated Sep. 6, 2005).
ASTM International, Annual Book of ASTM Standards, 8.02:208-211, 584-587 (1984).
Ansel et al., "Dosage Form Design: Pharmaceutical and Formulation Considerations,"*Pharmaceutical Dosage Forms and Drug Delivery Systems*, Ch. 3 at 87-92 (7$^{th}$ ed. Lippincott Williams & Wilkins 1999).
Ansel et al., "Modified-Release Dosage Forms and Drug Delivery Systems,"*Pharmaceutical Dosage Forms and Drug Delivery Systems*, Ch. 8 at 229-243 (7$^{th}$ ed. Lippincott Williams & Wilkins 1999).
Aulitzky, "Acute hematologic effects of interferon α, interferon γ, tumor necrosis factor α and Interleukin 2," Ann. Hemetol. 62(1):25-31 (Feb. 1991).
Hauck, "Engineer's Guide to Plastics," Materials Engineering 5(72):38-45 (Jul. 17, 1972).
Bailon et al., "Rational Design of a Potent, Long-lasting Form of Interferon: A 40 kDa Branched Polyethylene Glycol-conjugated Interferon Alpha-2a for the Treatment of Hepatitis C" Bioconjugate Chemistry 12(2):195-202 (2001).
Bakan et al., "Physicochemical Characterization of a Synthetic Lipid Emulsion for Hepatocyte-Selective Delivery of Lipophilic Compounds: Application to Polyiodinated triglycerides as Contrast Agents for Computed Tomography," J. Pharm. Sci., 85(9):908-914 (1996).
Bakhtiar et al, "Taking Delivery," Soap Perfumery & Cosmetics 76(3):59-65 (2003) (liposomes in cosmetic delivery systems).
Balkwill, "Interferons," Lancet 1(8646):1060-1063 (May 1989).
Bauer et al., "Non-aqueous emulsions as vehicles for capsule fillings," Drug Dev. & Industrial Pharmacy 10(5):699-712 (1984).
Bekkering et al., "Estimation of early hepatitis C viral clearance in patients receiving daily interferon and ribavirin therapy using a mathematical model," Hepatology 33(2):419-423 (Feb. 2001).
Bell et al, "Impact of moisture on thermally induced denaturation and decomposition of lyophilized bovine somatotropin," Drug Delivery Research & Dev. Biopolymers, (35):201-209 (1995).
Bell et al., "Hamster preproglucagon contains the sequence of glucagon and two related peptides," Nature 302:716-718 (1983).
Bertoncello et al., "Haematopoietic radioprotection by Cremophor EL: a polyethoxylated castor oil," Int. J. Radiat. Biol. 67(1):57-64 (1995).
Bohlinder et al., "Use and characteristics of a novel lipid particle-forming matrix as a drug-carrier system," Euro. J. Pharm. Sci. 2(4):271-279 (1994).
Bolinger et al., "Recombinant interferon γ for treatment of chronic granulomatous disease and other disorders," Clin. Pharm. 11(10):834-850 (Oct. 1992).
Bonkovsky et al., "Outcomes research in chronic viral hepatitis C: effects of interferon therapy," Can. J. Gastroenterol. 14(Supp. B):21B-29B (Jul.-Aug. 2000).
Borden et al., "Second-generation interferons for cancer: clinical targets," Semin. Cancer Biol. 10(2):125-144 (Apr. 2000).
Boue et al., "Antiviral and antiluteolytic activity of recombinant bovine IFN-ω1 obtained from Pichia pastoris," J. Interferon & Cytokine Res. 20:677-683 (2000).
Buckwold et. al. "Antiviral activity of CHO-SS cell-derived human omega interferon and other human interferons against HCV RNA replicons and related viruses," Antiviral Res. 73(2):118-25 (Feb. 2007) (Epub Sep. 11, 2006).
Cantor, "Theory of lipid monolayers comprised of mixtures of flexible and stiff amphiphiles in anthermal solvents: fluid phase coexistence," J. Chem. Physics 104(20):8082-8095 (1996).
Cas No. 56-81-5 (Nov. 16, 1984).
Chang et al., "Biodegradeable polyester implants and suspension injection for sustained release of a cognitive enhancer," Pharm. Tech. 20(1):80-84 (1996).
Chapman et al., "Physical Studies of Phospholipids. VI. Thermotropic and Lyotropic Mesomorphism of Some 1,2-Diacylphosphatidylcholines (lecithins)," Chem. & Physics of Lipids 1(5):445-475 (1967).
Chaumeil, "Micronization: a method of improving the bioavailability of poorly soluble drugs," Methods & Findings in Experimental & Clinical Pharmacology 20(3):211-215 (1998).
Clark et al., "The diabetic Zucker fatty rat," Proc. Soc. Exp. Biol. 173(1):68-75 (1983).
Condino-Neto, "Interferon-γ improves splicing efficiency of CYBB gene transcripts in an interferon responsive variant of chronic granulomatous disease due to a splice site consensus region mutation," Blood 95(11):3548-3554 (Jun. 2000).
Darney, "Subdermal progestin implant contraception," Current Opinion in Obstetrics & Gynecology 3:470-476 (1991).
Das et al., "Reviewing Antisense Oligonucleotide Therapy: Part 2, Delivery Issues," BioPharm. 2(11):44-51 (1999).
Davis et al., "Durability of viral response to interferon alone or in combination with oral ribavirin in patients with chronic hepatitis C," Prog. Abstr. 50th Annu. Mtg. Postgrad. Courses Am. Assn. Study Liver Dis., Dallas, TX, Abstract 570 (Nov. 5-9, 1999).
Desai et al., "Protein structure in the lyophilized state: a hydrogen isotope exchange/NMR study with bovine pancreatic trypsin inhibitor," J. Am. Chem. Soc. 116(21):9420-9422 (1994).
Di Marco et al., "Combined treatment of relapse of chronic hepatitis C with high-dose α-2B interferon plus ribavirin for 6 or 12 months," Prog. Abstr. 50th Annu. Mtg. Postgrad. Courses Am. Assn. Study Liver Dis., Dallas, TX, Abstract 569 (Nov. 5-9, 1999).
Dorr et al., "Phase I-II trial of interferon-alpha 2b by continuous subcutaneous infusion over 28 days," J. Interferon Res. 8:717-725 (1988).
Uhlig et al., "The electro-smotic acutation of implantable insulin micropumps," J. Biomed. Materials Res. 17:931-943 (1983).
Elias et al., "Infusional Interleukin-2 and 5-fluorouracil with subcutaneous interferon-α for the treatment of patients with advanced renal cell carcinoma: a southwest oncology group Phase II study," Cancer 89(3):597-603 (Aug. 2000).
Eppstein et al., "Biological activity of liposome-encapsulated murine interferon γ is mediated by a cell membrane receptor," PNAS USA 82:3688-3692 (1985).

(56) References Cited

OTHER PUBLICATIONS

Eros et al., "Multiple phase emulsions as controlled drug delivery therapeutic systems," Proc.-Conf. Colloid Chem. 193-196 (1993).
Fang et al., "The impact of baseline liver histology on virologic response to interferon α-2b±ρ ribavirin therapy in patients with chronic hepatitis C," Prog. Abstr. 50th Annu. Mtg. Postgrad. Courses Am. Assn. Study Liver Dis., Dallas, TX, Abstract 572 (Nov. 5-9, 1999).
Felker et al., "The Rate of Transfer of Unesterified Cholesterol from Rat Erythrocytes to Emulsions Modeling Nascent Triglyceride-Rich Lipoproteins and Chylomicrons Depends on the Degree of Fluidity of the Surface," J. Nutritional Biochem. 4(1):630-634 (1993).
Ferenci et al, "Combination of interferon (IFN) induction therapy and ribavirin in chronic hepatitis C," Prog. Abstr. Dig. Dis. Week 2000, San Diego, CA, Abstract 977 (May 21-24, 2000).
Fontaine et al., "Recovery from chronic hepatitis C in long-term responders to ribavirin plus interferon α," Lancet 356(9223):41 (Jul. 2000).
Franchetti et al., "Furanfurin and Thiophenfurin: Two Novel TiazofurinAnalogues. Synthesis, Structure, Antitumor Activity, and Interactions with Inosine Monophosphate Dehydrogenase" J. Medicinal Chem. 38(19):3829-3837 (1995).
Fujii et al., "Effect of phosphatidylcholine on Skin Permeation of Indomethacin from gel prepared with Liquid Paraffin and Hydrogenated Phospholipid," Int'l J. Pharmaceutics 222(1):57-64 (2001).
Fujii et al., "Enhancement of skin permeation of miconazole by phospholipid and dodecyl 2-(N, N-dimethylamino) propionate (Ddaip)," Int'l J. Pharmaceutics 234(12):121-128 (2002).
Luft et al., "Electro-osmotic valve for the controlled administration of drugs," Med. & Biological Engineering & Computing 45-50 (Jan. 1978) (non-English with English abstract).
Gan to Kagaku Ryoho, "Phase II study of recombinant leukocyte α interferon (Ro22-8181) in malignant brain tumors," Cancer & Chemotherapy 12(4):913-920 (Apr. 1985) (non-English with English abtract).
Gappa et al., "Juvenile laryngeal papillomatosis—a case report," Pneumologie 45(11):936-938 (Nov. 1991) (X0009079028) (non-English with English abstract).
Gause et al., "Phase I study of subcutaneously administered interleukin-2 in combination with interferon alfa-2a in patients with advanced cancer" J. Clin. Oncol. 14(8):2234-2241 (Aug. 1996).
Glue et al., "A dose-ranging study of Peg-intron and ribavirin in chronic hepatitis C—safety, efficacy, and virological rationale," Prog. Abstr. 50th Annu. Mtg. Postgrad. Courses Am. Assn. Study Liver Dis., Dallas, TX, Abstract 571 (Nov. 5-9, 1999).
Gonzales et al., "Randomized controlled trial including an initial 4-week 'induction' period during one year of high-dose interferon α-2B treatment for chronic hepatitis C," Prog. Abstr. Dig. Dis. Week 2000, San Diego, CA, Abstract 975 (May 21-24, 2000).
Gosland et al., "A phase I trial of 5-day continuous infusion cisplatin and interferon alpha," Cancer Chemother. Pharmacol. 37(1-2):39-46 (1995).
Grant et al., "Combination therapy with interferon-α plus N-acetyl cystein for chronic hepatitis C: a placebo controlled double-blind multicentre study," J. Med. Virol. 61(4):439-442 (Aug. 2000).
Hageman, "The Role of Moisture in Protein Stability, " Drug Dev. & Ind. Pharm. 14(14):2047-2070 (1988).
Heathcote et al., "Peginterferon alfa-2a in Patients With Chronic Hepatitis C and Cirrhosis," New England J. Med. 343(23):1673-1680 (2000).
Heim et al., "Intracellular signaling and antiviral effects of interferons," Dig. Liver Dis. 32(3):257-263 (Apr. 2000).
Hellstrand et al., "Histamine and cytokine therapy," Acta Oncol. 37(4):347-353 (1998).
Hellstrand et al., "Histamine and the response to IFN-α in chronic hepatitis C," Interferon Cytokine Res. 18(1):21-22 (Jan. 1998).
Hellstrand et al., "Histamine in immunotherapy of advanced melanoma: a pilot study," Cancer Immunol Immunother. 39(6):416-419 (Dec. 1994).

Hisatomi et al., "Toxicity of polyoxyethylene hydrogenated castor oil 60 (HCO-60) in experimental animals," J. Toxicol. Sci., 18(3):1-9 (1993).
Hodoshima, N. et al., "Lipid nanoparticles for delivering antitumor drugs," International Journal of Pharmaceutics, 146(1):81-92 (1997).
Hoffmann-La Roche Inc., Pegasys® (peginterferon alfa-2a), 15 pages (2002).
Horton et al., "Antitumor effects of interferon-omega: in vivo therapy of human tumor xenografts in nude mice," Cancer Res 59(16):4064-4068 (Aug. 1999).
Hubel et al., "A phase I/II study of idarubicin, dexamethasone and interferon-alpha (1-Dexa) in patients with relapsed or refractory multiple myeloma" Leukemia 11(Suppl 5):547-551 (Dec. 1997).
Jacobelli et al., "A phase I study of recombinant interferon-alpha administered as a seven-day continuous venous infusion at circadian-rhythm modulated rate in patients with cancer" Am. J. Clin. Oncol. 18(1):27-31 (1995).
IFNB Multiple Sclerosis Study Group, "Interferonβ-1b is effective in relapsing-remitting multiple sclerosis," Neurology 43(4):655-667 (Apr. 1993).
Intermune® Inc., Infergen® (Interferon alfacon-1), 5 pages (2002).
Introduction to Antibodies, http ://www.chemicon.com/resource/ANT101/a1.asp, 8 pages (retrieved May 2, 2007).
Isaacs et al., "Virus interference. I. The interferon," Pro. R. Soc. Lond. B. Biol. Sci. 147:258-267 (1957).
Jain et al., "Controlled delivery of drugs from a novel injectable in situ formed biodegradable PLGA microsphere system," J. Microencapsulation 17(3):343-362 (2000).
Jordan et al., "Guidelines for Antiemetic Treatment of Chemotherapy-Induced Nausea and Vomiting: Past, Present and Future Recommendations," the Oncologist 12(9):1143-1150 (2007).
Kabalnov et al., "Macroemulsion type and stability of alkane-water-phospholipid systems," Abstracts of Papers, Part 1, 210th ACS National Meeting, 0/8412-3222-9, American Chemical Society, Chicago, IL (Aug. 20-24, 1995) (Abstract only).
Kabalnov et al., "Phospholipids as Emulsion Stabilizers.2. Phase Behavior Versus Emulsion Stability," Journal of Colloid and Interface Science 184(1):227-235 (1996).
Khalili et al., "Interferon and ribavirin versus interferon and amantadine in interferon nonresponders with chronic hepatitis C," Am. J. Gastroenterol. 95(5):1284-1289 (May 2000).
Kildsig et al., "Theoretical Justification of Reciprocal Rate Plots in Studies of Water Vapor Transmission through Films," J. Pharma. Sci. 29(11):1634-01637 (Nov. 17, 1970).
Kirkwood et al., "Interferon alfa-2b adjuvant therapy of high-risk resected cutaneous melanoma: The Eastern Cooperative Oncology Group Trial EST 1684," J. Clin. Oncol. 14(1):7-17 (1996).
Kita et al., "Characterization of a polyethylene glycol conjugate of recombinant human interferon-γ," Drug Des. Deliv. 6(3):157-0167 (Sep. 1990).
Knepp et al, "Identification of antioxidants for prevention of peroxide-mediated oxidation of recombinant human ciliary neurotrophic factor and recombinant human nerve growth factor," J. Pharm. Sci. Tech. 50(3):163-171 (1996).
Knepp et al., "Stability of nonaqueous suspension formulations of plasma derived factor IX and recombinant human alpha interferon at elevated temperatures," Pharma. Res. 15(7):1090-1095 (1998).
Knobler et al., "Systemic α-interferon therapy of multiple sclerosis," Neurology 34(10):1273-1279 (Oct. 1984).
Kovacevic et al., "Treatment of chronic viral hepatitis B in secondary membranoproliferative glomerulonephritis using recombinant α-2 interferon," Maksic Dj Vojnosanit. Pregl. 57(2):235-240 (Mar.-Apr. 2000) (non-English with English abstract).
Kracke et al., "Mx proteins in blood leukocytes for monitoring interferon β-1b therapy in patients with MS," Neurology 54(1):193-199 (Jan. 2000).
Kronenberger et al., "Influence of interferon-α on CD82-expression in HCV-positive patients," Prog. Abstr. Dig. Dis. Week 2000, San Diego, CA, Abstract 976 (May 21-24, 2000).
Krown et al., "Interferons and interferon inducers in cancer treatment," Semin. Oncol. 13(2):207-217 (1986).

(56) References Cited

OTHER PUBLICATIONS

Kubes et al., "Cross-species antiviral and antiproliferative activity of human interferon-ω," J. Interferon Res. 14:57-59 (1994).
Kunzi et al., "Role of interferon-stimulated gene ISG-15 in the interferon-ω-mediated inhibition of human immunodeficiency virus replication," J. Interferon Cytokine Res. 16(11):919-927 (Nov. 1996).
Larsson, "Stability of emulsions formed by polar lipids," Progress in the Chemistry of Fats and Other Lipids 16:163-0169 (1978).
Lee et al., "Dynamics of hepatitis C virus quasispecies turnover during interferon-A treatment," Prog. Abstr. Dig. Dis. Week 2000, San Diego, CA, Abstract 974 (May 21-24, 2000).
Lee, "Therapy of hepatits C: interferon alfa-2A trials," Hepatology 26: 89S-95S (Sep. 1997) (XP000981288).
Lukaszewski et al., "Pegylated α interferon is an effective treatment for virulent Venezuelan equine encephalitis virus and has profound effects on host immune response to infection," J. Virol. 74(11):5006-5015 (Jun. 2000).
Lundberg, "A submicron lipid emulsion coated with amphipathic polyethylene glycol for parenteral administration of paclitaxel (Taxol)," J. Pharm. & Pharmacol. 49(1):16-21 (1997).
Magnuson et al. "Enhanced recovery of a secreted mammalian protein from suspension culture of genetically modified tobacco cells," Protein Expression & Purification 7:220-228 (1996).
Malley et al., "Chronic Toxicity and Oncogenicity of N-Methylpyrrolidone (Nmp) in Rats and Mice by Dietary Administration," Drug Chem Toxicol. 24(4):315-38 (Nov. 2001).
Manning et al, "Stability of protein pharmaceuticals," Pharm. Res. 6(11):903-918 (1989).
Marincola et al., "Combination therapy with interferon alfa-2a and interleukin-2 for the treatment of metastatic cancer," J. Clinical Oncol. 13(5):1110-1122 (1995) (XP009078965).
Massey, "Interaction of vitamin E with saturated phospholipid bilayers," Biochem. & Biophys. Res. Comms. 106(3):842-847 (1982).
Mchutchison et al., "Interferon α-2b alone or in combination with ribavirin as initial treatment for chronic hepatitis C," N. Engl. J. Med. 339(21):1485-1492 (Nov. 1998).
Mchutchison, et al., "Open-label phase 1B study of hepatitis C viral dynamics with omega interferon treatment," Hepatology 34(4):A333 (Oct. 1, 2001) (X0004716177) (Abstract Only).
Merad et al., "Generation of monocyte-derived dendritic cells from patients with renal cell cancer: modulation of their functional properties after therapy with biological response modifiers (IFN-α plus IL-2 and IL-12)," J. Immunother. 23(3):369-378 (May-Jun. 2000).
Milella et al., "Neutralizing antibodies to recombinant α-interferon and response to therapy in chronic hepatitis C infection," Liver 13(3):146-150 (Jun. 1993).
Mohler, "Primer on electrodeposited coatings," Materials Engineering 5:38-45 (1972).
Morgan, "Structure and Moisture Permeability of Film-Forming Poloyers," Ind. Eng. Chem. 45(10):2296-2306 (1953).
Motzer et al., "Phase I trial of 40-kd branched pegylated interferon alfa-2a for patients with advanced renal cell carcinoma," J. Clinical Oncol. 19(5):1312-1319 (2001).
Neumann et al., "IIepatitis C Viral Dynamics in Vivo and the Antiviral Efficacy of Interferon-alpha Therapy," Science 282:103-107 (Dec. 1998).
Nieforth et al., "Use of an indirect pharmacodynamic stimulation model of MX protein induction to compare in vivo activity of interferon-α-2a and a polyethylene glycol-modified derivative in healthy subjects," Clin. Pharmacol. Ther. 59(6):636-646 (Jun. 1996).
Norden et al., "Physicochemical characterization of a drug-containing phospholipid-stabilized o / w emulsion for intravenous administration," Eur. J. Pharm. Sci. 13(4):393-401 (2001).
Olaso et al., "Early prediction of lack of response to treatment with interferon and interferon plus ribavirin using biochemical and virological criteria in patients with chronic hepatitis C," Esp. Quimioter. 12(3):220-228 (Sep. 1999) (non-English with English abstract).
Ortiz, A. et al., "A differential scanning calorimetry study of the interaction of α tocopherol with mixtures of phospholipids," Biochim et Biophys Acta 898(2):214-222 (1987).
Panitch, "Interferons in multiple sclerosis," Drugs 44(6):946-962 (Dec. 1992).
Pimstone et al., "High dose (780 MIU/52 weeks) interferon monotherapy is highly effective treatment for hepatitis C," Prog. Abstr. Dig. Dis. Week 2000, San Diego, CA, Abstract 973 (May 21-24, 2000).
Plauth et al, "Open-label phase II study of omega interferon in previously untreated HCV infected patients," Hepatology 34(4):A331 (Oct. 1, 2001) (X004716169) (Abstract Only).
Plauth et al, "Open-label study of omega interferon in previously untreated HCV-infected patients," J. Hepatology 36(Supp. 1):125 (Apr. 2002) (X0002511882) (Abstract Only).
Poynard et al., "Is an 'a la carte' combined interferon α 2b plus ribavirin possible for the first line treatment in patients with chronic hepatitis C," Hepatology 31(1):211- 218 (Jan. 2000).
Poynard et al., "Randomized trial of interferon α 2b plus ribavirin for 48 weeks or for 24 weeks versus interferon α 2b plus placebo for 48 weeks for the treatment of chronic infection with hepatitis C virus," Lancet 352(9138):1426-1432 (Oct. 1998).
Quesada et al., *Interferons in Hematological Malignancies* at 487-495 (eds. Baron et al., U. Tex. 1987).
Quintanar-Guerrero et al., "Applications of the ion-pair concept to hydrophilic substances with special emphasis on peptides," Pharm. Res. 14(2):119-127 (1997).
Rajkuiviar et al., "Phase I evaluation of radiation combined with recombinant interferon alpha-2a and BCNU for patients with high-grade glioma," Int'l J. Radiat. Oncol. Biol. Phys. 40(2):297-302 (Jan. 15, 1998).
Roche Pharmaceuticals, Roferon® -A (Interferon alfa-2a, recombinant), 22 pages (2003).
Roff et al., "Handbook of Common Polymers," 72 pages (Cleveland Rubber Co. 1971).
Rogers et al., "Permeability Valves," Ind. & Eng. Chem. 49(11):1933-1936 (Nov. 17, 1957).
Roman et al., "Cholestasis in the rat by means of intravenous administration of cyclosporine vehicle, Cremophor EL," Transplantation 48(4);554-558 (1989).
Roth et al., "High Dose Etretinate and Interferon-alpha—A Phase I Study in Squamous Cell Carcinomas and Transitional Cell Carcinomas," Acta Oncol. 38(5):613-617 (1999).
Roth et al., "Combination therapy with amylin and peptide YY[3-36] in obese rodents: anorexigenic synergy and weight loss additivity," Endocrinol. 148(12):605461 (Dec. 2007).
Schering Corp., Intron® A for Injection, 6 pages (2001).
Schering Corp., PEG-Intron™ (Peginterferon alfa-2b) Powder for Injection, 29 pages (2003).
Schmalfub, et al., "Modification of drug penetration into human skin using microemulsions," J. Controlled Release 46(3):279-285 (1997).
Sen et al., "The interferon system: a bird's eye view of its biochemistry," J. Biol. Chem. 267(8):5017-5020 (Mar. 1992).
Shiffman et al., "A decline in HCV-RNA level during interferon or ihterferon/ribavirin therapy in patients with virologic nonresponse is associated with an improvement in hepatic histology," Prog. Abstr. 50th Annu. Mtg. Postgrad. Courses Am. Assn. Study Liver Dis., Dallas, TX, Abstract 567 (Nov. 5-9, 1999).
Shima et al., "Serum total bile acid level as a sensitive indicator of hepatic histological improvement in chronic hepatitis C patients responding to interferon treatment," J. Gastroenterol. Hepatol. 15(3):294-299 (Mar. 2000).
Shiratori et al., "Histologic improvement of fibrosis in patients with hepatitis C who have sustained response to interferon therapy," Ann. Int. Med. 132(7):517-524 (Apr. 2000).
Simon et al., "A longitudinal study of T1 hypointense lesions in relapsing MS:MSCRG trial of interferon β1a," Neurology 55(2):185-192 (Jul. 2000).

(56) References Cited

OTHER PUBLICATIONS

Sulkowski et al., "Pegylated Interferon Alfa-2A (Pegasys™) and Ribavirin Combination Therapy for Chronic Hepatitis C: A Phase II Open-Label Study" Gastroenterology 118(4, Supp. 2), Abstract 236 (2000).

Sulkowski et al., "Peginterferon-α-2a (40kD) and ribavirin in patients with chronic hepatitis C: a phase II open label study," Biodrugs 16(2):105-109 (2002).

Talpaz et al., "Phase I study of polyethylene glycol formulation of interferon alpha-2B (Schering 54031) in Philadelphia chromosome-positive chronic myelogenous leukemia," Blood 98(6):1708-1713 (2001).

Talsania et al., "Peripheral exendin-4 and peptide YY(3-36) synergistically reduce food intake through different mechanisms in mice," Endocrinology 146(9):3748-56 (Sep. 2005).

Tanaka et al., "Effect of interferon therapy on the incidence of hepatocellular carcinoma and mortality of patients with chronic hepatitis C: a retrospective cohort study of 738 patients," Int. J. Cancer 87(5):741-749 (Sep. 2000).

Tong et al., "Prediction of response during interferon α 2b therapy in chronic hepatitis C patients using viral and biochemical characteristics: a comparison," Hepatology 26(6):1640-01645 (Dec. 1997).

Touza Rey et al., "The clinical response to interferon-γ in a patient with chronic granulomatous disease and brain abscesses due to Aspergillus fumigatus," Ann. Med. Int. 17(2):86-87 (Feb. 2000).

Trudeau et al., "A phase I study of recombinant human interferon alpha-2b combined with 5-fluorouracil and cisplatin in patients with advanced cancer" Cancer Chemother. Pharmacol. 35(6):496-500 (1995).

Tsung et al., "Preparation and Stabilization of Heparin/Gelatin Complex Coacervate Microcapsules," J. Pharm. Sci. 86(5):603-7 (May 1997).

Unniappan et al., "Effects of dipeptidyl peptidase IV on the satiety actions of peptide YY," Diabetologia; Clinical and Experimental Diabetes and Metabolism 49(8):1915-1923 (Jun. 27, 2006).

Vokes et al., "A phase I trial of concomitant chemoradiotherapy with cisplatin dose intensification and granulocyte-colony stimulating factor support for advanced malignancies of the chest," Cancer Chemother. Pharmacol. 35(4):304-312 (1995).

Wang et al., "Preferential interaction of α-tocopherol with phosphatidylcholines in mixed aqueous dispersions of phosphatidylcholine and phosphatidylethanolamine," Eur. J. Biochem. 267(21):6362-6368 (2000).

Wang et al., "Ripple phases induced by α-tocopherol in saturated diacylphosphatidylcholines," Archives of Biochem. & Biophys. 377(2):304-314 (2000).

Wang et al., "The distribution of α-tocopherol in mixed aqueous dispersions of phosphatidylcholine and phosphatidylethanolamine," Biochimica et Biophysica Acta-Biomembranes 1509(1-2):361-372 (2000).

Wang et al, "Parenteral formulations of proteins and peptides: stability and stabilizers," J. Parenter. Sci. Technol. 42(2S):S4-S26 (1988).

Weinstock-Guttman et al., "What is new in the treatment of multiple sclerosis?" Drugs 59(3):401-410 (Mar. 2000).

Weissmann et al., "The interferon genes," Prog. Nucleic Acid Res. Mol. Biol. 33:251-300 (1986).

Wright et al., "Preliminary experience with α-2b-interferon therapy of viral hepatitis in liver allograft recipients," Transplantation 53(1):121-123 (Jan. 1992).

Young et al., "Glucose-lowering and insulin-sensitizing actions of exendin-4: studies in obese diabetic (ob/ob, db/db) mice, diabetic fatty Zucker rats, and diabetic rhesus monkeys (Macaca mulatta)," Diabetes, 48(5):1026-1034 (1999).

Younossi et al., "The role of amantadine, rimantadine, ursodeoxycholic acid, and NSAIDs, alone or in combination with α interferons, in the treatment of chronic hepatitis C," Semin. Liver Dis. 19(Supp. 1):95-102 (1999).

Yu et al., "Preparation, characterization, and in vivo evaluation of an oil suspension of a bovine growth hormone releasing factor analog," J. Pharm. Sci. 85(4):396-401 (1996).

Zeidner et al., "Treatment of FeLV-induced immunodeficiency syndrome (feLV-FAIDS) with controlled release capsular implantation of 2',3'-dideoxycytidine," Antivir. Res. 11(3):147-160 (Apr. 1989).

Zein, "Interferons in the management of viral hepatitis," Cytokines Cell Mol. Ther. 4(4):229-241 (Dec. 1998).

Zeuzem et al., "Peginterferon Alfa-2a in Patients with Chronic Hepatitis C," New Engl. J. Med. 343(23):1666-1672 (2000).

Zeuzem et al., "Hepatitis C virus dynamics in vivo: effect of ribavirin and interferon α on viral turnover," Hepatology 28(1):245-252 (Jul. 1998).

Zhang et al., "Report on Large Dosage Interferon to Treat 30 Cases of Viral Encephalitis," J. Clinical Pediatrics 14(2):83-84 (1996).

Zhang et al, "A new strategy for enhancing the stability of lyophilized protein: the effect of the reconstitution medium on keratinocyte growth factor," Pharm. Res. 12(10):1447-1452 (1995).

Zheng et al. "Therapeutic Effect of Interferon Varied Dose in Treating Virus Encephalitis," Beijing Med. J. 13(2):80-81 (1998).

Ziesche et al., "A preliminary study of long-term treatment with interferon γ-1b and low-dose prednisolone in patients with idiopathic pulmonary fibrosis," New Engl. J. Med. 341(17):1264-1269 (Oct. 1999).

Adolf, "Human interferon omega-a review," Mult. Sclr. 1:S44-47 (1995).

Costantino et al., "Protein Spray Freeze Drying. 2. Effect of Formulation Variables on particle Size and Stability," J. Pharm. Sci. 91:388-395 (2002).

Henry et al., "Comparing ITCA 650, continuous subcutaneous delivery of exenatide via DUROS® device, vs. twice daily exenatide injections in metformin-treated type 2 diabetes," 21 pages (oral presentation at the 46th Annual Meeting of the European Association for the Study of Diabetes in Stockholm, Sweden, Sep. 20-24, 2010).

Huggins et al., "Synergistic antiviral effects of ribavirin and the C-nucleoside analogs tiazofurin and selenazofurin against togaviruses, bunyaviruses, and arenaviruses," Antimicrobial Agents & Chemotherapy, 26(4):476-480 (1984).

Ishiwata et al., "Clinical effects of the recombinant feline interferon-omega on experimental parvovirus infection in beagle dogs," J. Vet. Med. Sci. 60(8):911-917 (1998).

Johnson et al., "How interferons fight disease," Sci. Am. 270(5):68-75 (May 1994).

Lublin et al., "Defining the clinical course of multiple sclerosis: results of an internatinal survey," Neurology. 46:907-911 (1996).

Madsbad, "Exenatide and liraglutide: different approaches to develop GLP-1 receptor agonists (incretin mimetics)—preclinical and clinical results," Best Practice & Research Clinical Endocrinology & Metabolism 23:463-77 (2009).

Nielsen, "Incretin mimetics and DPP-IV inhibitors for the treatment of type 2 diabetes," Drug Discovery Today 10(10):703-710 (May 15, 2005).

Palmeri et al., "5-Fluorouracil and recombinant α-interferon-2a in the treatment of advanced colorectal carcinoma: a dose optimization study," J. Chemotherapy 2(5):327-330 (Oct. 1990).

Patti et al., "Natural interferon-b treatment of relapsing-remitting and secondary-progressive multiple sclerosis patients: two-year study," Acta. Neurol. Scand. 100:283-289 (1990).

Paty et al., "Interferon beta-1 b is effective in relapsing-remitting multple sclerosis," Neurology 43:662-667 (1993).

PCT International Search Report for PCT/US2009/000916, 4 pages (Aug. 12, 2009).

Quianzon et al., "Lixisenatide-Once-daily Glucagon-like Peptide-1 Diabetes," US Endocrinology 7(2):104-109 (2011).

Ratner et al., "Dose-dependent effects of the one-daily GLP-1 receptor agonist lixisenatide in patients with Type 2 diabetes inadequately controlled with metfmmin: a randomized, double-blind, placebo-controlled trial," Diabetic Medicine 27(9):1024-1032 (Sep. 2010).

Roberts et al., "The Evolution of the Type I Interferonsl," J. Interferon Cytokine Res. 18(10):805-816 (Oct. 1998).

(56) References Cited

OTHER PUBLICATIONS

Rohloff et al., "Duros Technology Delivers Peptides and Proteins at Consistent Rate Continuously for 3 to 12 Months," J. Diabetes Sci. & Tech., 2(3):461-467 (May 1, 2008).

Sequence Listings for International Patent Application Publication No. WO2009109927, WIPO Patentscope, 1 page (last visited Nov. 14, 2012), available at http://patentscope.wipo.int/search/docservicepdf_pct!id00000008776887.

Shire et al., "Challenges in the Development of High Protein Concentration Formulations," J. Pharm. Sci. 93:1390-1402 (2004).

Smith, "Peripheral Neuro-hormones as a Strategy to Treat Obesity," pages 1-35 (oral presentation at the 2007 Cardiometabolic Health Congress in Boston, MA, Sep. 26-29, 2007).

Written Opinion for International Patent Application No. PCT/US2009/005629 (Apr. 15, 2011) (corresponding to U.S. Appl. No. 12/587,946).

Zhang et al., "Efficacy observations of different dosages of interferon to treat 150 Hepatitis B carriers," Current Physician 2(12):45-46 (1997).

\* cited by examiner

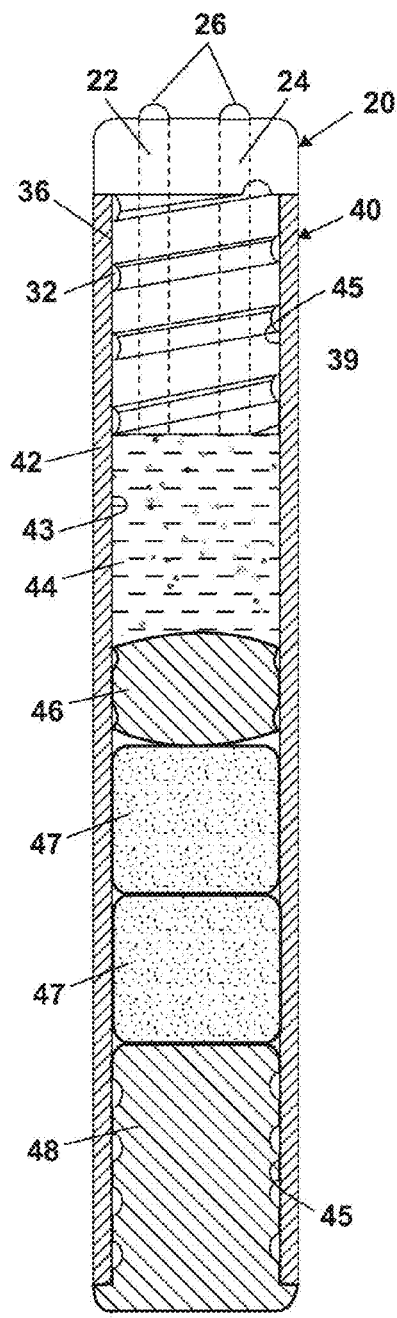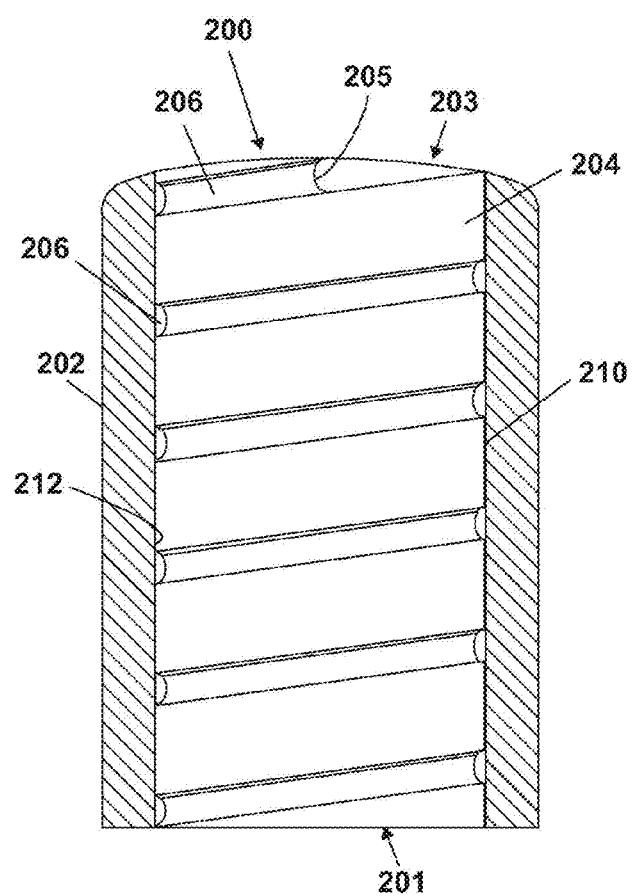
(PRIOR ART)
FIG. 1
FIG. 2A

TWO-PIECE, INTERNAL-CHANNEL OSMOTIC DELIVERY SYSTEM FLOW MODULATOR

CROSS-REFERENCE TO RELATED APPLICATIONS

The present application claims a priority benefit as a continuation (CON) of U.S. non-provisional patent application Ser. No. 13/898,358, entitled "Two-Piece, Internal-Channel Osmotic Delivery System Flow Modulator," filed on May 20, 2013, and issued as U.S. Pat. No. 8,992,962 on Mar. 31, 2015, the content of which is incorporated herein by reference in its entirety.

U.S. non-provisional application Ser. No. 13/898,358 claims a priority benefit as a continuation (CON) of U.S. non-provisional patent application Ser. No. 13/740,187, entitled "Two-Piece, Internal-Channel Osmotic Delivery System Flow Modulator," filed on Jan. 12, 2013, and issued as U.S. Pat. No. 8,470,353 on Jun. 25, 2013, the content of which is incorporated herein by reference in its entirety.

U.S. non-provisional application Ser. No. 13/740,187 claims a priority benefit as a continuation (CON) of U.S. non-provisional patent application Ser. No. 13/601,939, entitled "Two-Piece, Internal-Channel Osmotic Delivery System Flow Modulator," filed on Aug. 31, 2012, and issued as U.S. Pat. No. 8,367,095 on Feb. 5, 2013, the content of which is incorporated herein by reference in its entirety.

U.S. non-provisional application Ser. No. 13/601,939 claims a priority benefit as a continuation (CON) of U.S. non-provisional patent application Ser. No. 13/433,287, entitled "Two-Piece, Internal-Channel Osmotic Delivery System Flow Modulator," filed on Mar. 29, 2012, and issued as U.S. Pat. No. 8,273,365 on Sep. 25, 2012, the content of which is incorporated herein by reference in its entirety.

U.S. non-provisional application Ser. No. 13/433,287 claims a priority benefit as a continuation (CON) of U.S. non-provisional patent application Ser. No. 13/209,328, entitled "Two-Piece, Internal-Channel Osmotic Delivery System Flow Modulator," filed on Aug. 12, 2011, and issued as U.S. Pat. No. 8,158,150 on Apr. 17, 2012, the content of which is incorporated herein by reference in its entirety.

U.S. non-provisional application Ser. No. 13/209,328 claims a priority benefit as a division (DIV) of U.S. non-provisional patent application Ser. No. 11/755,494, entitled "Two-Piece, Internal-Channel Osmotic Delivery System Flow Modulator," filed on May 30, 2007, and issued as U.S. Pat. No. 8,052,996 on Nov. 8, 2011, the content of which is incorporated herein by reference in its entirety.

U.S. non-provisional application Ser. No. 11/755,494 claims a priority benefit from U.S. provisional application Ser. No. 60/809,451, entitled "Two-Piece, Internal-Channel Osmotic Delivery System Flow Modulator," filed on May 30, 2006, the content of which is incorporated herein by reference in its entirety.

U.S. non-provisional application Ser. No. 11/755,494 also claims a priority benefit as a continuation-in-part (CIP) of U.S. non-provisional patent application Ser. No. 11/347,562, entitled "Solvent/Polymer Solutions as Suspension Vehicles," filed on Feb. 3, 2006, and issued as U.S. Pat. No. 8,114,437 on Feb. 14, 2012, the content of which is incorporated herein by reference in its entirety.

U.S. non-provisional application Ser. No. 11/347,562 claims a priority benefit from U.S. provisional application Ser. No. 60/650,225, entitled "Solvent/Polymer Solutions as Suspension Vehicles," filed on Feb. 3, 2005, the content of which is incorporated herein by reference in its entirety.

BACKGROUND OF THE INVENTION

The invention relates generally to osmotic delivery systems for sustained delivery of active agents in fluid environments. More particularly, the invention relates to a flow modulator for delivering an active agent from an osmotic delivery system in a fluid environment.

FIG. 1 illustrates a prior-art osmotic delivery system 40, as described in U.S. Pat. No. 6,524,305 issued to Peterson et al. The osmotic delivery system 40 includes an enclosure 42 containing osmotic agent 47 and active agent 44. A dividing member 46 forms a partition between the osmotic agent 47 and the active agent 44. A semipermeable plug 48 is inserted into a first opening 45 of the enclosure 42. The semipermeable plug 48 selectively permits fluid to enter the interior of the enclosure 42. A flow modulator 20 is inserted into a second opening 39 of the enclosure 42. The flow modulator 20 allows the active agent 44 to exit the interior of the enclosure 42 while controlling back-diffusion of fluids into the interior of the enclosure 42. When the osmotic delivery system 40 is disposed in a fluid environment, fluid from the exterior of the enclosure 42 enters the enclosure 42 through the semipermeable plug 48 and permeates the osmotic agent 47, causing the osmotic agent 47 to swell. The osmotic agent 47 displaces the dividing member 46 as it swells, causing an amount of the active agent 44 to be delivered to the environment of use through the flow modulator 20.

In the prior-art osmotic delivery system 40 shown in FIG. 1, the outer surface of the flow modulator 20 includes a helical delivery path 32 through which the active agent 44 passes from the interior to the exterior of the enclosure 42. The thread 36 which defines the helical delivery path 32 abuts the interior surface 43 of the enclosure 42 so that the active agent 44 comes into contact with the interior surface 43 of the enclosure 42 as it passes through the helical delivery path 32. The pitch, amplitude, cross-sectional area, and shape of the helical delivery path 32 are selected such that back-diffusion into the enclosure 42 from the fluid environment is minimized. Fill hole 22 and vent hole 24 are provided in the flow modulator 20. When assembling the osmotic delivery system 40, the flow modulator 20 is first inserted in the enclosure 42. The active agent 44 is then injected into the enclosure 42 through the fill hole 22, while gases in the enclosure 42 escape through the vent hole 24. Thereafter, caps 26 are inserted in the holes 22, 24 so that delivery of the active agent 44 occurs only through the helical delivery path 32.

From the foregoing, there continues to be a desire to provide additional reliability and flow modulator capabilities in osmotic delivery systems.

SUMMARY OF THE INVENTION

In one aspect, the invention relates to an osmotic delivery system flow modulator which comprises an outer shell constructed and arranged for positioning in an opening of a reservoir of an osmotic delivery system, an inner core inserted in the outer shell, and a fluid channel having a spiral shape defined between the outer shell and the inner core, the fluid channel being adapted for delivery of an active agent formulation from the reservoir of the osmotic delivery system.

In another aspect, the invention relates to an osmotic delivery system which comprises a reservoir, a semipermeable plug disposed at a first end of the reservoir to selectively permit flow into the reservoir, a flow modulator disposed at a second end of the reservoir, the flow modulator comprising an internal spiral channel adapted for delivery of an active agent formulation contained in the reservoir to a fluid environment in which the osmotic delivery system operates.

In yet another aspect, the invention relates to an implantable delivery system for an active agent formulation which comprises a reservoir made of an impermeable material, a first chamber in the reservoir containing an osmotic engine, a second chamber in the reservoir containing an active agent formulation, a semipermeable plug disposed at a first end of the reservoir adjacent the first chamber, and a flow modulator as described above disposed at a second end of the reservoir adjacent the second chamber.

Other features and advantages of the invention will be apparent from the following description and the appended claims.

BRIEF DESCRIPTION OF THE DRAWINGS

The accompanying drawings, described below, illustrate typical embodiments of the invention and are not to be considered limiting of the scope of the invention, for the invention may admit to other equally effective embodiments. The figures are not necessarily to scale, and certain features and certain view of the figures may be shown exaggerated in scale or in schematic in the interest of clarity and conciseness.

FIG. 1 depicts a cross-sectional view of a prior-art osmotic delivery system.

FIG. 2A depicts a partial cross-sectional view of a flow modulator having an inner core inserted in an outer shell and an internal spiral fluid channel formed in the inner core.

DETAILED DESCRIPTION OF THE INVENTION

Figure 2C:
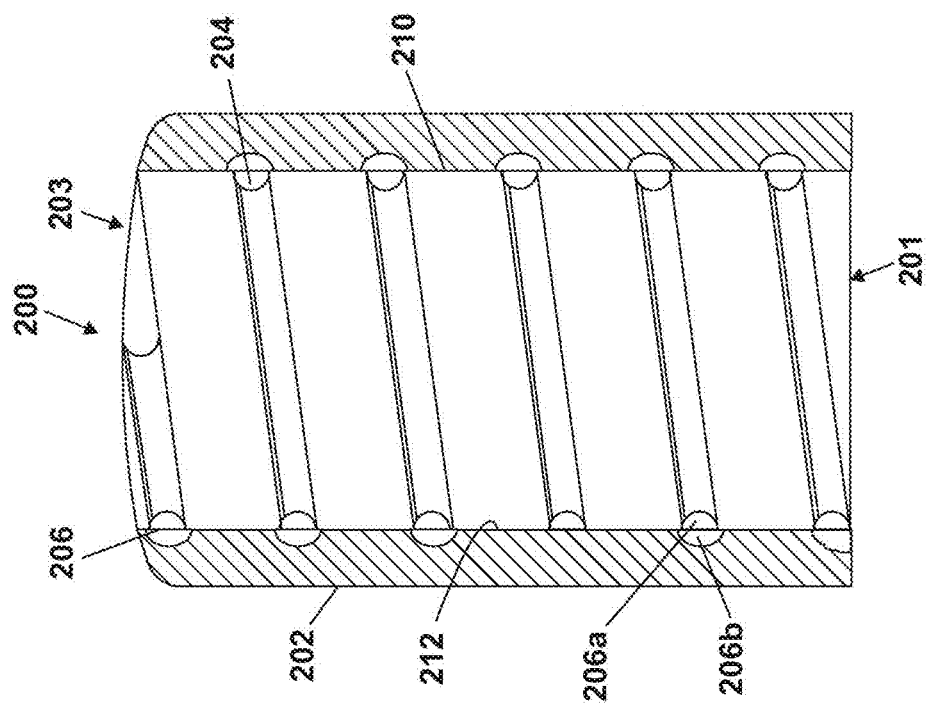
FIG. 2C depicts a partial cross-sectional view of a flow modulator having an inner core inserted in an outer shell and an internal spiral fluid channel formed in the inner core and the outer shell.

The invention will now be described in detail with reference to a few preferred embodiments, as illustrated in the accompanying drawings. In describing the preferred embodiments, numerous specific details are set forth in order to provide a thorough understanding of the invention. However, it will be apparent to one skilled in the art that the invention may be practiced without some or all of these specific details. In other instances, well-known features and/or process steps have not been described in detail so as not to unnecessarily obscure the invention. In addition, like or identical reference numerals are used to identify common or similar elements.

FIGS. 2A through 2E depict partial cross-sectional views of a flow modulator 200 for delivery of an active agent formulation from a reservoir of an osmotic delivery system. Referring to FIG. 2A, the flow modulator 200 has an inlet side 201, which is the side that would be exposed to the active agent formulation in the reservoir of the osmotic delivery system, and an outlet side 203, which is the side that would be exposed to a fluid environment in which the osmotic delivery system operates. Typically, the fluid environment is an aqueous environment, that is, the fluid environment contains water. The flow modulator 200 includes an outer shell 202 and a generally cylindrical inner core 204 inserted in the outer shell 202. Extending from the inlet side 201 to the outlet side 203 of the flow modulator 200, between the outer shell 202 and the inner core 204, is a fluid channel 206 having a spiral shape. All or a substantial portion of the fluid channel 206 may have a spiral shape. The fluid channel 206 is internal to the flow modulator 200. The flow modulator 200 therefore forms a barrier between active agent formulation passing through the fluid channel 206 and the reservoir of the osmotic delivery system.

Figure 2B:
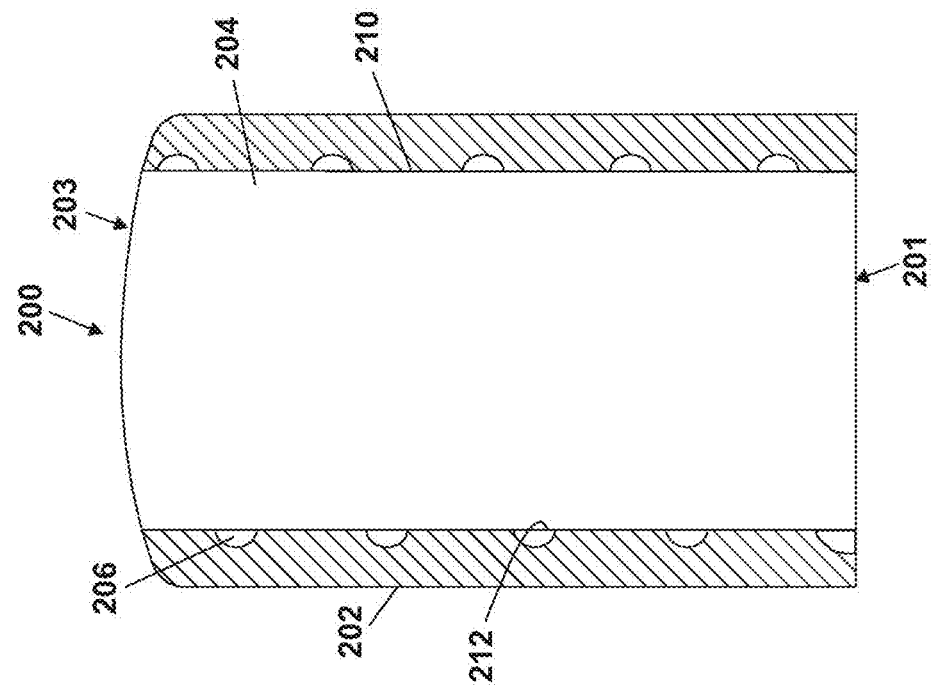
FIG. 2B depicts a partial cross-sectional view of a flow modulator having an inner core inserted in an outer shell and an internal spiral fluid channel formed in the outer shell.
Figure 2E:
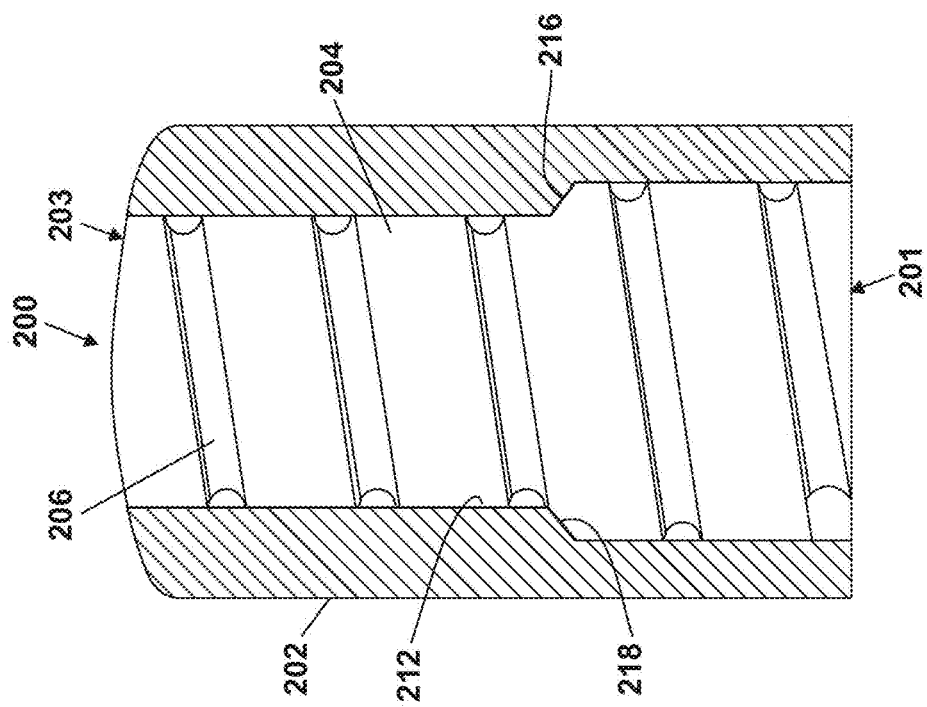
FIG. 2E depicts a partial cross-section view of a flow modulator having an inner core inserted in an outer shell and mating surfaces on the inner core and outer shell for preventing expulsion of the inner core from the outer shell.
Figure 2D:
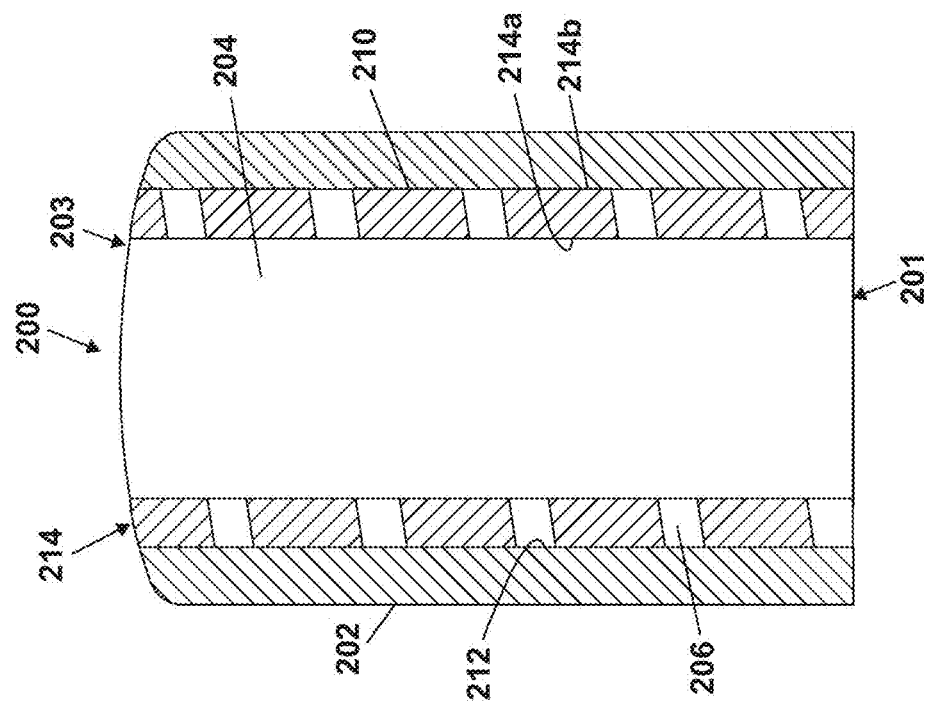
FIG. 2D depicts a partial cross-sectional view of a flow modulator having an inner core inserted in an outer shell and a flow insert including an internal spiral fluid channel interposed between the inner core and the outer shell.

In FIGS. 2A-2C, the outer surface 210 of the inner core 204 mates with the inner surface 212 of the outer shell 202. The fluid channel 206 may be formed in the outer surface 210 of the inner core 204, as shown in FIG. 2A, or in the inner surface 212 of the outer shell 202, as shown in FIG. 2B. Alternatively, as shown in FIG. 2C, the fluid channel 206 may include a first fluid channel 206a formed in the outer surface 210 of the inner core 204 and a second fluid channel 206b formed in the inner surface 212 of the outer shell 202, wherein the first fluid channel 206a and the second fluid channel 206b are adjacent to each other or in communication. All or a substantial portion of each of the fluid channels 206a, 206b has a spiral shape. Alternatively, as shown in FIG. 2D, a flow insert 214 may be disposed between the outer surface 210 of the inner core 204 and the inner surface 212 of the outer shell 202, wherein the flow insert 214 provides the fluid channel 206. The flow insert 214 may be a coiled tube, for example, wherein the spaces between the coils of the tube serve as the fluid channel 206. Alternatively, the flow insert 214 may be a hollow cylindrical body or a sleeve in which a spiral groove is formed, where the spiral groove serves as the fluid channel 206. The fluid channel 206 may have any desired cross-section, examples of which include circular or D shape. D-shaped fluid channels are shown in FIGS. 2A-2E. The length of the fluid channel 206 depends on the configuration of the osmotic delivery system and the desired release rate. Typically, the (spiral) length of the fluid channel 206 ranges from 10 to 50 mm. Typically, the effective cross-sectional diameter of the fluid channel 206 ranges from 0.1 to 0.5 mm. These ranges are given as examples and are not intended to limit the invention as otherwise described herein.

Referring to FIGS. 2A-2D, the largest outer diameter of the inner core 204 and the largest inner diameter of the outer shell 202 are selected such that there is an interference fit or a seal between the outer surface 210 of the inner core 204 and the inner surface 212 of the outer shell 202. This interference fit or seal confines the flow of formulation to the fluid channel 206. This interference fit or seal may be sufficient to prevent expulsion of the inner core 204 and/or flow insert 214 from the outer shell 202. On the other hand, in FIGS. 2A-2C, the mating portion of the surfaces 210, 212 of the inner core 204 and outer shell 202, respectively, may include features such as threaded connection, bonded connection, welded connection, and the like to additionally secure the inner core 204 to the outer shell 202. In FIG. 2D, similar connection features may be formed between the portions of the inner and outer surfaces 214a, 214b of the flow insert 214 which mate with the surfaces 210, 212 of the inner core 204 and outer shell 202, respectively. FIG. 2E discloses an alternate method for preventing expulsion of the inner core 204 from the outer shell 202 which includes an outer shoulder 216 on the outer surface 210 of the inner core 204 abutting/engaging an inner shoulder 218 on the inner surface 212 of the outer shell 202. This prevents expulsion of the inner core 204 through the outlet side 203 of the flow modulator 200. The abutting/engaging surfaces of the shoulders 216, 218 may be flat or may be tapered, as shown in FIG. 2E.

The use of abutting/engaging shoulders 216, 218 to prevent expulsion of the inner core 204 from the outer shell 202 into the fluid environment in which the osmotic delivery system operates may be applied to any of the examples shown in FIGS. 2A-2D. Further, any of the features of the examples shown in FIGS. 2A-2E may be interchanged and combined to make alternate examples of the flow modulator 200. For example, in FIG. 2E, a channel having a spiral shape may also be located in the inner surface 212 of the outer shell 202, as described in FIG. 2C. Or, in FIG. 2D, channels having a spiral shape may also be located in the inner surface 212 of the outer shell 202 and/or outer surface 210 of the inner core 204, as described in FIGS. 2A and 2B, respectively, where the channels in the outer shell 202 and/or inner core 204 would be adjacent to or in communication with the fluid channel 206 in the flow insert 214.

Referring to FIGS. 2A-2E, the outer shell 202, the inner core 204, and the flow insert 214 are preferably formed from a material that is inert and biocompatible. Examples of inert, biocompatible materials include, but are not limited to, non-reactive polymers and metals such as titanium, stainless steel, platinum and their alloys, and cobalt-chromium alloys. Non-reactive polymers are useful where it is desirable to avoid interaction between the active agent formulation and a metallic material as the active agent formulation is delivered to the fluid environment in which the osmotic delivery system operates. Examples of suitable non-reactive polymers include, but are not limited to, polyaryletherketones, such as polyetheretherketone and polyaryletheretherketone, ultra-high molecular weight polyethylene, fluorinated ethylene-propylene, polymethylpentene, and liquid crystal polymers. Preferably, at least the surfaces of the outer shell 202, the inner core 204, and the flow insert 214 which would be exposed to the active agent formulation as the active agent formulation flows through the fluid channel 206 are made of or coated with a material that would not have a detrimental effect on the active agent formulation. In a preferred example, the aforementioned surfaces are made of a non-metallic material that is inert and biocompatible. Such non-metallic material could be a non-reactive polymer, examples of which are given above.

The length, the cross-sectional shape, and flow area of the fluid channel 206 may be selected such that the average linear velocity of the active agent formulation through the fluid channel 206 is higher than that of the linear inward influx of materials due to diffusion or osmosis from the fluid environment in which the osmotic delivery system operates. This would have the effect of attenuating or moderating back diffusion, which if not controlled could contaminate the active agent formulation in the osmotic delivery system. The release rate of the active agent formulation can be modified by modifying the geometry of the fluid channel 206, as described below.

The convective flow of an active agent through the fluid channel 206 is determined by the pumping rate of the osmotic delivery system and the concentration of the active agent in the active agent formulation in the reservoir of the osmotic delivery system. The convective flow may be expressed as follows:

$$Q_{ca} = (Q)(C_a) \tag{1}$$

where $Q_{ca}$ is the convective transport of beneficial in mg/day, Q is the overall convective transport of the active agent formulation in cm$^3$/day, and $C_a$ is the concentration of active agent in the active agent formulation within the reservoir of the osmotic delivery system in mg/cm$^3$.

The diffusive flow of active agent out of the fluid channel 206 is a function of active agent concentration and diffusivity and cross-sectional shape and length of the fluid channel 206. The diffusive flow may be expressed as follows:

$$Q_{da} = \frac{D\pi r^2 \Delta C_a}{L} \tag{2}$$

where $Q_{da}$ is the diffusive transport of the active agent in mg/day, D is the diffusivity through the fluid channel 206 in cm$^2$/day, r is the effective inner radius of the fluid channel 206 in cm, $\Delta C_a$ is the difference between the concentration of the active agent in the active agent formulation in the reservoir of the osmotic delivery system and the concentration of the active agent in the fluid environment outside of the delivery orifice 205 of the flow modulator 200 in mg/cm$^3$, and L is the (spiral) length of the fluid channel 206 in cm.

In general, the concentration of active agent in the active agent formulation in the osmotic delivery system is much greater than the concentration of the active agent in the fluid environment of use such that the difference, $\Delta C_a$ can be approximated by the concentration of the active agent within the active agent formulation in the osmotic delivery system, $C_a$. Thus:

$$Q_{da} = \frac{D\pi r^2 \Delta C_a}{L} \tag{3}$$

It is generally desirable to keep diffusive flux of the active agent much less than convective flow of the active agent. This is represented as follows:

$$\frac{Q_{da}}{Q_{ca}} = \frac{D\pi r^2 C_a}{Q C_a L} = \frac{D\pi r^2}{QL} < 1 \tag{4}$$

Equation (4) indicates that the relative diffusive flux decreases with increasing volumetric flow rate and path length, increases with increasing diffusivity and channel radius, and is independent of active agent concentration.

The diffusive flux of water where the fluid channel 206 opens into the osmotic delivery system can be approximated as follows:

$$Q_{wd}(\text{res}) = C_0 Q_e^{(-QL/D_w A)} \tag{5}$$

where $C_o$ is the concentration profile of water in mg/cm$^3$, Q is the mass flow rate in mg/day, L is the length of the fluid channel 206 in cm, $D_w$ is the diffusivity of water through the material in the fluid channel 206 in cm²/day, and A is the cross-sectional area of the fluid channel 206 in cm².

The hydrodynamic pressure drop across the delivery orifice can be calculated as follows:

$$\Delta P = \frac{8QL\mu}{\pi r^4} \quad (6)$$

where Q is the mass flow rate in mg/day, L is the length of the spiral fluid channel in cm, μ is the viscosity of the formulation, and r is the effective inner radius of the fluid channel in cm.

Figure 3:
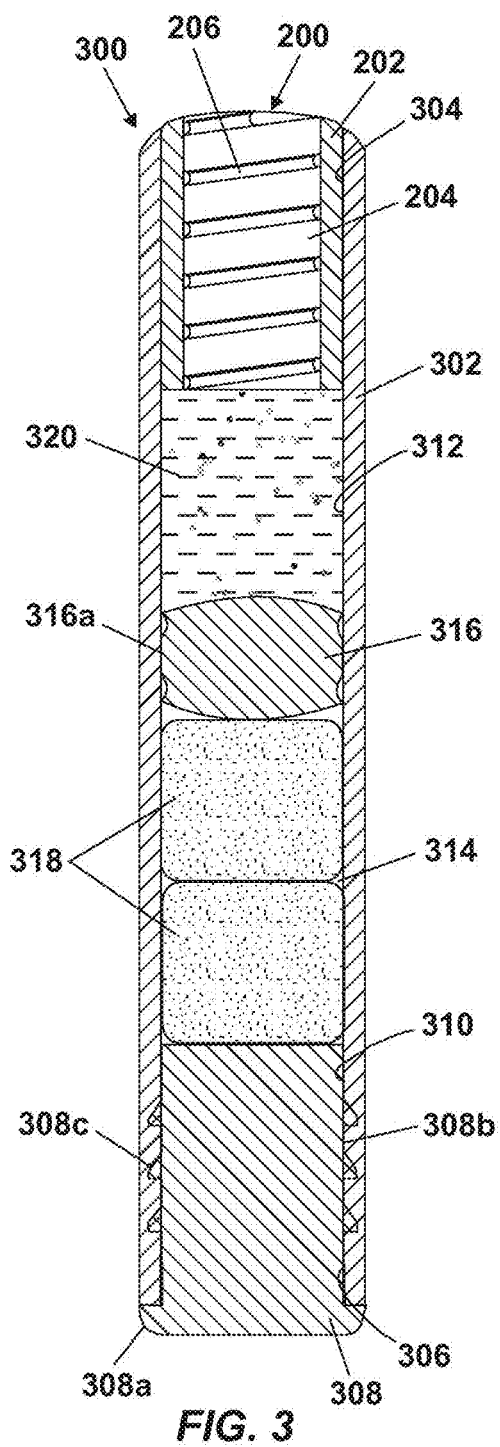
FIG. 3 depicts a cross-sectional view of an osmotic delivery system with the flow modulator of FIG. 2A.

FIG. 3 shows an osmotic delivery system 300 including the flow modulator 200. Although the osmotic delivery system 300 is shown with the flow modulator 200 of FIG. 2A, it should be clear that any of the flow modulators 200 shown in FIGS. 2A-2E may be used with the osmotic delivery system 300. The osmotic delivery system 300 includes a reservoir 302, which may be sized such that it can be implanted within a body. The reservoir 302 has open ends 304, 306. The flow modulator 200 is inserted in the open end 304. A semipermeable plug 308 is inserted in the open end 306.

The semipermeable plug 308 is a membrane that controls rate of flow of fluid from the fluid environment in which the osmotic delivery system operates into the reservoir 302. The semipermeable plug 308 allows fluid from the fluid environment to enter the reservoir 302. Compositions in the reservoir 302 are prevented from flowing out of the reservoir 302 through the semipermeable plug 308 because of the semipermeable nature of the semipermeable plug 308. The semipermeable plug 308 may be inserted partially or fully into the open end 306. In the former case, the semipermeable plug 308 may include an enlarged end portion 308a which acts as a stop member engaging an end of the reservoir 302. The outer surface 308b of the semipermeable plug 308 may have protrusions or ribs 308c that engage the inner surface 310 of the reservoir 302, thereby locking the semipermeable plug 308 to the reservoir 302 and allowing a seal to be formed between the reservoir 302 and the semipermeable plug 308. The reservoir 302 may also include undercuts which receive the protrusions 308c on the semipermeable plug 308. Semipermeable materials for the semipermeable plug 308 are those that can conform to the shape of the reservoir 302 upon wetting and that can adhere to the inner surface 310 of the reservoir 302. Typically, these materials are polymeric materials, which can be selected based on the pumping rates and system configuration requirements. Examples of suitable semipermeable materials include, but are not limited to, plasticized cellulosic materials, enhanced polymethyl methacrylates (PMMAs) such as hydroxyethylmethacrylate (HEMA), and elastomeric materials, such as polyurethanes and polyamides, polyether-polyamind copolymers, thermoplastic copolyesters, and the like. Polyurethanes are generally preferred.

Two chambers 312, 314 are defined inside the reservoir 302. The chambers 312, 314 are separated by a partition 316, such as a slidable piston or flexible diaphragm, which is configured to fit within and make sealing contact with the reservoir 302 and to move or deform longitudinally within the reservoir 302. Preferably, the partition 316 is formed of an impermeable resilient material. As an example, the partition 316 may be a slidable piston made of an impermeable resilient material and may include annular ring shape protrusions 316a that form a seal with the inner surface 310 of the reservoir 302. Osmotic engine 318 is disposed in the chamber 314 adjacent the semipermeable plug 308, and an active agent formulation 320 is disposed in the chamber 312 adjacent the flow modulator 200. The partition 316 isolates the active agent formulation 320 from the environmental fluids that are permitted to enter the reservoir 302 through the semipermeable plug 308 such that in use, at steady-state flow, the active agent formulation 320 is expelled through the fluid channel 206 at a rate corresponding to the rate at which fluid from the fluid environment flows into reservoir 302 through the semipermeable plug 308.

The osmotic engine 318 may be in the form of tablets as shown. One or more such tablets may be used. Alternatively, the osmotic engine 318 may have other shape, texture, density, and consistency. For example, the osmotic engine 318 may be in powder or granular form. The osmotic engine 318 may include an osmopolymer. Osmopolymers are hydrophilic polymers that can imbibe aqueous fluids, such as water and biological fluids, and upon imbibing aqueous fluids swell or expand to an equilibrium state and retain a significant portion of the imbibed fluid. Osmopolymers swell or expand to a very high degree, usually exhibiting 2 to 50 fold volume increase. Osmopolymers may or may not be cross-linked. Preferred osmopolymers are hydrophilic polymers that are lightly cross-linked, such cross-links being formed by covalent or ionic bonds or residue crystalline regions after swelling. Osmopolymers can be of plant, animal or synthetic origin. Examples of osmopolymers or hydrophilic polymers suitable for use in the osmotic engine 318 include, but are not limited to, poly (hydroxy-alkyl methacrylate) having a molecular weight of from 30,000 to 5,000,000; polyvinylpyrrolidone (PVP) having a molecular weight of from 10,000 to 360,000; anionic and cationic hydrogels; polyelectrolytes complexes; polyvinyl alcohol having a low acetate residual, cross-linked with glyoxal, formaldehyde, or glutaraldehyde and having a degree of polymerization of from 200 to 30,000, a mixture of methyl cellulose, cross-linked agar and carboxymethyl cellulose; a mixture of hydroxypropyl methylcellulose and sodium carboxymethylcellulose; a mixture of hydroxypropyl ethylcellulose and sodium carboxymethyl cellulose; sodium carboxymethylcellulose; potassium carboxymethylcellulose; a water insoluble, water swellable copolymer formed from a dispersion of finely divided copolymer of maleic anhydride with styrene, ethylene, propylene, butylene or isobutylene cross-linked with from 0.001 to about 0.5 moles of saturated cross-linking agent per mole of maleic anhydride per copolymer; water swellable polymers of N-vinyl lactams; polyoxyethylene-polyoxypropylene gel; polyoxybutylene-polyethylene block copolymer gel; carob gum; polyacrylic gel; polyester gel; polyuria gel; polyether gel; polyamide gel; polycellulosic gel; polygum gel; and initially dry hydrogels that imbibe and absorb water which penetrates the glassy hydrogel and lowers its glass temperature. Other examples of osmopolymers include polymers that form hydrogels, such as CARBOPOL®, acidic carboxypolymer, a polymer of acrylic and cross-linked with a polyallyl sucrose, also known as carboxypolymethylene and carboxyvinyl polymer having a molecular weight of 250,000 to 4,000,000; CYNAMER® polyacrylamides; cross-linked water swellable indene-maleic anhydride polymers; GOOD-RITE® polyacrylic acid having a molecular weight of 80,000 to 200,000; POLYOX® polyethylene oxide polymer having a molecular weight of 100,000 to 5,000,000 and higher; starch graft copolymers; AQUA-KEEPS® acrylate polymer polysaccharides composed of condensed glucose units such as diester cross-linked polygluran; and the like. The osmotic engine 318 may also include an osmagent either in addition to or in lieu of the osmopolymer. Osmagents include inorganic and organic compounds that exhibit an osmotic pressure gradient across a semipermeable wall against an external fluid. Osmagents imbibe fluid into the osmotic system, thereby making available fluid to push against the formulation for delivery through the flow modulator. Osmagents are also known as osmotically effective compounds or solutes. Osmagents useful in the osmotic engine 318 include magnesium sulfate, magnesium chloride, sodium chloride, potassium sulfate, sodium sulfate, lithium sulfate, potassium acid phosphate, mannitol, urea, inositol, magnesium succinate, tartaric acid, carbohydrates such as raffinose, sucrose, glucose, lactose, sorbitol, and mixtures thereof.

The active agent formulation 320 may include one or more active agents. The active agent may be any physiologically or pharmacologically active substance, particularly those known to be delivered to the body of a human or an animal, such as medicaments, vitamins, nutrients, or the like. Active agents which may be delivered by the osmotic delivery system 300 through the flow modulator 200 include, but are not limited to, drugs that act on infectious diseases, chronic pain, diabetes, the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, proteins, enzymes, hormones, polynucleotides, nucleoproteins, polysaccharides, glycoproteins, lipoproteins, polypeptides, steroids, analgesics, local anesthetics, antibiotic agents, anti-inflammatory corticosteroids, ocular drugs and synthetic analogs of these species. Preferred active agents include macromolecules (proteins and peptides) and active agents that are highly potent. The active agent can be present in a wide variety of chemical and physical forms, such as solids, liquids and slurries. In addition to the one or more active agents, the formulation 320 may optionally include pharmaceutically acceptable carriers and/or additional ingredients such as antioxidants, stabilizing agents, buffers, and permeation enhancers.

Materials that are used for the reservoir 302 should be sufficiently rigid to withstand expansion of the osmotic engine 318 without changing its size or shape. Further, the materials should ensure that the reservoir 302 will not leak, crack, break, or distort under stress to which it could be subjected during implantation or under stresses due to the pressures generated during operation. The reservoir 302 may be formed of inert, biocompatible, natural or synthetic materials which are known in the art. The material of the reservoir 302 may or may not bioerodible. A material that is bioerodible will at least in part dissolve, degrade, or otherwise erode in the fluid environment of use. Preferably, the material of the reservoir 302 is non-bioerodible. Generally, preferred materials for the reservoir 302 are those acceptable for human implantation. Preferably, the material of the reservoir 302 is impermeable, particularly when stability of the formulation in the reservoir 302 is sensitive to the fluid environment of use. Examples of materials suitable for the reservoir 302 include non-reactive polymers or biocompatible metals or alloys. Examples of non-reactive polymers for the reservoir 302 include, but are not limited to, acrylonitrile polymers such as acrylonitrile-butadiene-styrene terpolymer; halogenated polymers such as polytetraflouroethylene, polychlorotrifluoroethylene, copolymer tetrafluoroethylene and hexafluoropropylene; polyimide; polysulfone; polycarbonate; polyethylene; polypropylene; polyvinylchloride-acrylic copolymer; polycarbonate-acrylonitrile-butadiene-styrene; and polystyrene. Examples of metallic materials for the reservoir 302 include, but are not limited to, stainless steel, titanium, platinum, tantalum, gold, and their alloys, as well as gold-plated ferrous alloys, platinum-plated ferrous alloys, cobalt-chromium alloys and titanium nitride coated stainless steel. For size-critical applications, high payload capability, long duration applications, and applications where the formulation is sensitive to body chemistry at the implantation site, the reservoir 302 is preferably made of titanium or a titanium alloy having greater than 60%, often greater than 85% titanium.

The diameter of the flow modulator 200 may be selected such that the flow modulator 200 can be press-fitted into the open end 304 of the reservoir 302. It is also possible to include features such as threads on the outer surface 220 of the outer shell 202 and the inner surface 310 of the reservoir 302 for securing the flow modulator 200 to the reservoir 302.

The following examples are illustrative of the invention and are not to be construed as limiting the invention as otherwise described herein.

An osmotic delivery system, as illustrated in FIG. 3, containing interferon-omega (IFN-ω) for the treatment of, for example, hepatitis C was assembled from the following components: (i) reservoir made of implant grade titanium alloy and having undercuts at an end thereof, (ii) osmotic engine including two cylindrical tablets, each tablet including primarily sodium chloride salt with cellulosic and povidone binders, (iii) piston, (iv) semipermeable plug made of polyurethane and having retaining ribs that mate with undercuts in reservoir, (v) flow modulator having a spiral internal flow channel with a D-shaped cross-section, a diameter of 0.25 mm, and a spiral length of 35 mm, and (vi) a suspension formulation including a particle formulation of IFN-ω suspended in a non-aqueous vehicle.

Figure 4:
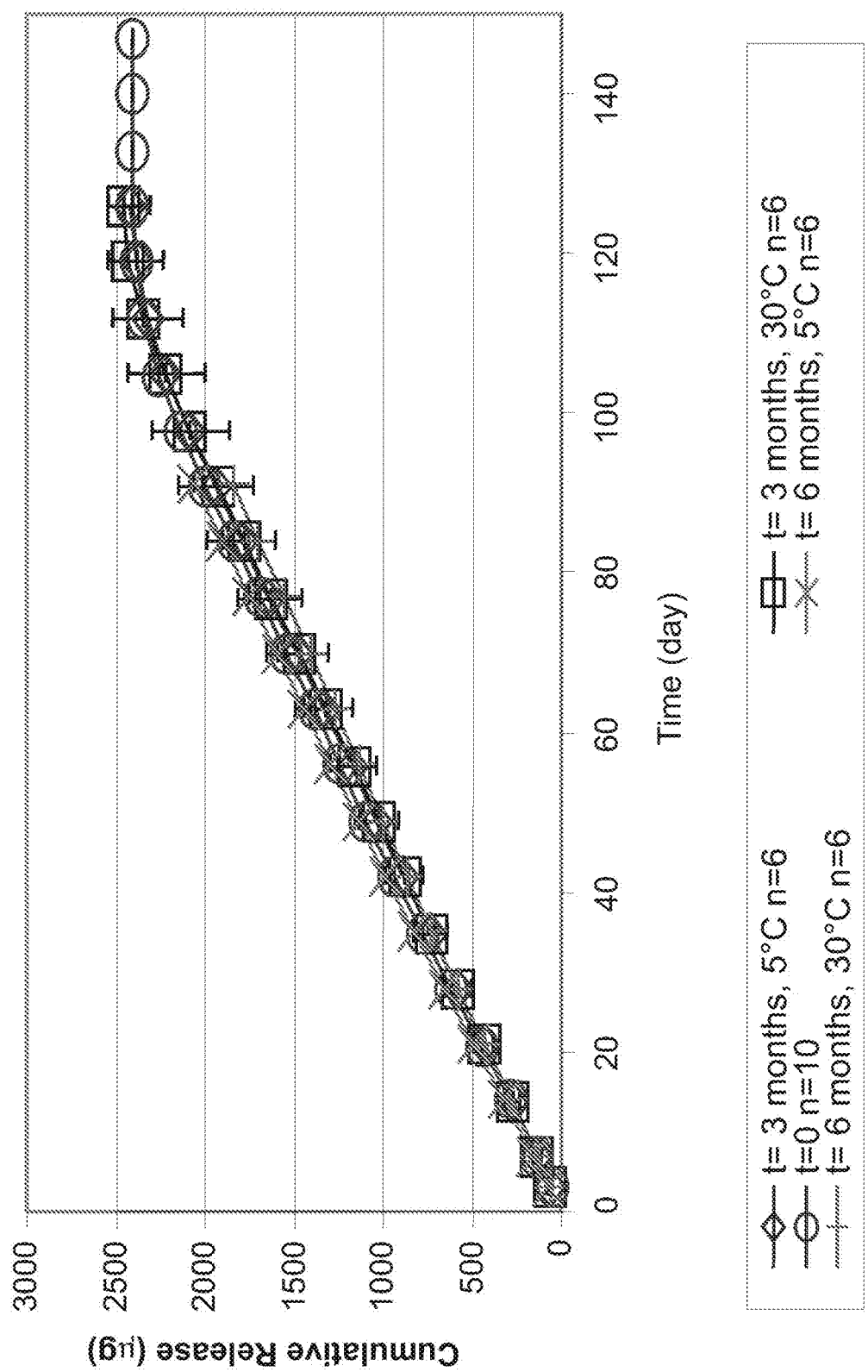
FIG. 4 depicts an in vitro cumulative release of an active agent using an osmotic delivery system according to FIG. 3.

Reservoirs of several osmotic delivery systems, as described above, were filled with 150-μL of the suspension formulation. The semipermeable plug ends of the osmotic delivery systems were placed into glass vials filled with phosphate buffer solution (PBS), and the flow modulator ends of the osmotic delivery systems were placed into glass vials filled with an aqueous release media. The systems were stored or incubated at 5° C. or 30° C., respectively. At specified time points, the release media was removed and exchanged for fresh solution. The sampled release media was analyzed for active agent content using Reversed Phase High Performance Liquid Chromatography (RP-HPLC). FIG. 4 shows in vitro cumulative release of IFN-ω over 6 months.

The invention may provide the following advantages. The two-piece flow modulator enables flexibility in design and manufacturability of the flow modulator. The outer shell is not integral with the reservoir and enables the channel in the flow modulator to be inspected prior to insertion of the flow modulator in the reservoir. The two-piece flow modulator minimizes additional mechanical forces on the channel during insertion of the flow modulator in the reservoir. The two-piece flow modulator enables flexibility to optimize the dimensions of the fluid channel by changing the channel on the inner core or flow insert while maintaining a common outer sleeve.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A process of making a flow modulator for an osmotic delivery system, comprising:
   forming an outer shell member and an inner core member from at least one non-metallic, nonreactive polymer material, the outer shell member comprising an inlet end, an outlet end, and an inner surface defining an internal volume for receiving the inner core member, the inner core member comprising an outer surface for engaging with the inner surface of the outer shell member when the inner core member is disposed in the internal volume, wherein at least one groove is formed in at least one of:
      the inner surface of the outer shell member such that the at least one groove extends from the inlet end to the outlet end and at least a portion of the at least one groove has a helical shape around an axis from the inlet end to the outlet end; and
      the outer surface of the inner core member such that when the inner core member is disposed in the internal volume, the at least one groove extends from the inlet end to the outlet end and at least a portion of the at least one groove has a helical shape around the axis from the inlet end to the outlet end; and
   disposing the inner core member in the internal volume such that the outer surface of the inner core member sealingly engages the inner surface of the outer shell member and the at least one groove defines at least one fluid channel between the inner surface of the outer shell member and the outer surface of the inner core member such that the at least one fluid channel extends from the inlet end to the outlet end and at least a portion of the at least one fluid channel has a helical shape around the axis from the inlet end to the outlet end.

2. The method of claim 1, wherein at least one first groove is formed in the inner surface of the outer shell member and at least one second groove is formed in the outer surface of the inner core member such that when the inner core member is disposed in the internal volume, the at least one first groove complements the at least one second groove.

3. The method of claim 1, at least one non-metallic, nonreactive polymer material is at least one of a polyaryletherketone, an ultra-high molecular weight polyethylene, a fluorinated ethylene-propylene, a polymethylpentene, and a liquid crystal polymer.

4. The method of claim 3, wherein the polyaryletherketone is at least one of polyetheretherketone and polyaryletheretherketone.

5. The method of claim 1, wherein:
   the inner core member further comprises an outer shoulder;
   the outer shell member further comprises an inner shoulder; and
   disposing the inner core member in the internal volume comprises engaging the outer shoulder and the inner shoulder to prevent expulsion of the inner core member from the outer shell member.

6. The method of claim 1, wherein the at least one groove is formed only in the inner surface of the outer shell member such that when the inner core member is disposed in the internal volume, the at least one groove extends from the inlet end to the outlet end and at least a portion of the at least one groove has a helical shape around the axis from the inlet end to the outlet end.

7. The method of claim 1, wherein the at least one groove is formed only in the outer surface of the inner core member such that when the inner core member is disposed in the internal volume, the at least one groove extends from the inlet end to the outlet end and at least a portion of the at least one groove has a helical shape around the axis from the inlet end to the outlet end.

8. The method of claim 1, wherein the at least one groove is formed only in the outer surface of the inner core member such that when the inner core member is disposed in the internal volume, the at least one groove extends from the inlet end to the outlet end and at least a portion of the at least one groove has a helical shape around the axis from the inlet end to the outlet end.

9. A method for mitigating back diffusion in an osmotic delivery system for an active agent formulation, the osmotic delivery system including a reservoir, a slidable piston defining within the reservoir a first chamber containing an osmotic engine and a second chamber containing the active agent formulation, and a semipermeable plug disposed at a first end of the reservoir adjacent the first chamber, the method comprising:
   providing an outer shell member and an inner core member, the outer shell member comprising an inlet end, an outlet end, and an inner surface defining an internal volume for receiving the inner core member, the inner core member comprising an outer surface for engaging with the inner surface of the outer shell member when the inner core member is disposed in the internal volume, wherein at least one groove is formed in at least one of:
      the inner surface of the outer shell member such that the at least one groove extends from the inlet end to the outlet end and at least a portion of the at least one groove has a helical shape around an axis from the inlet end to the outlet end; and
      the outer surface of the inner core member such that when the inner core member is disposed in the internal volume, the at least one groove extends from the inlet end to the outlet end and at least a portion of the at least one groove has a helical shape around the axis from the inlet end to the outlet end;
   assembling a flow modulator by disposing the inner core member in the internal volume such that the outer surface of the inner core member sealingly engages the inner surface of the outer shell member and the at least one groove defines at least one fluid channel between the inner surface of the outer shell member and the outer surface of the inner core member such that the at least one fluid channel extends from the inlet end to the outlet end and at least a portion of the at least one fluid channel has a helical shape around the axis from the inlet end to the outlet end; and
   positioning the flow modulator in an opening at a second end of the reservoir adjacent the active agent formulation in the osmotic delivery system such that by disposing the osmotic delivery system in a fluid environment, an amount of the active agent formulation is delivered to the fluid environment through the at least one fluid channel, the at least one fluid channel mitigating any back diffusion.

10. The method of claim 9, wherein at least one first groove is formed in the inner surface of the outer shell member and at least one second groove is formed in the outer surface of the inner core member such that when the inner core member is disposed in the internal volume, the at least one first groove complements the at least one second groove.

11. The method of claim 9, wherein the flow modulator is at least one of press-fitted into the opening at the second end of the reservoir and secured to the second end of the reservoir with one or more threads.

12. The method of claim 9, wherein the at least one groove is formed only in the inner surface of the outer shell member such that when the inner core member is disposed in the internal volume, the at least one groove extends from the inlet end to the outlet end and at least a portion of the at least one groove has a helical shape around the axis from the inlet end to the outlet end.

13. A method for regulating a release rate of an active agent formulation from an osmotic delivery system, the osmotic delivery system including a reservoir, a slidable piston defining within the reservoir a first chamber containing an osmotic engine and a second chamber containing the active agent formulation, a semipermeable plug disposed at a first end of the reservoir adjacent the first chamber, and an outer shell member disposed at a second end of the reservoir adjacent the active agent formulation, the outer shell comprising an inlet end, an outlet end, and an inner surface defining an internal volume for receiving an inner core member, the method comprising:

providing one or more inner core members, each inner core member comprising an outer surface for engaging the inner surface of the outer shell member when the inner core member is disposed in the internal volume, wherein at least one groove is formed in the outer surface of each inner core member such that when the inner core member is disposed in the internal volume, the at least one groove extends from the inlet end to the outlet end and at least a portion of the at least one groove has a helical shape around the axis from the inlet end to the outlet end;

selecting one of the one or more inner core members based on a geometry of the at least one groove; and assembling a flow modulator by disposing the selected inner core member in the internal volume such that the outer surface of the selected inner core member sealingly engages the inner surface of the outer shell member and the at least one groove defines at least one fluid channel between the inner surface of the outer shell member and the outer surface of the selected inner core member such that the at least one fluid channel extends from the inlet end to the outlet end and at least a portion of the at least one fluid channel has a helical shape around the axis from the inlet end to the outlet end, such that by disposing the osmotic delivery system in a fluid environment, the active agent formulation is delivered to the fluid environment through the at least one fluid channel at a release rate based at least in part on the geometry of the at least one groove.

14. The method of claim 13, wherein the active agent comprises a protein or a peptide.

15. The method of claim 13, wherein the geometry of the at least one groove includes a path length, an effective cross-sectional diameter of the at least one fluid channel defined by the at least one groove, and a cross-sectional shape of the at least one fluid channel defined by the at least one groove.

16. The method of claim 15, wherein the path length ranges from about 10 mm to about 50 mm.

17. The method of claim 16, wherein the path length is about 35 mm.

18. The method of claim 15, wherein the effective cross-sectional diameter ranges from about 0.1 mm to about 0.5 mm.

19. The method of claim 18, wherein the effective cross-sectional diameter is about 0.25 mm.

20. The method of claim 15, wherein the cross-sectional shape is at least one of a circular shape and a D-shape.

21. The method of claim 13, wherein the one or more inner core members comprise a plurality of inner core members, and the geometry of the at least one groove differs between each of the plurality of inner core members.

22. The method of claim 13, further comprising:
disengaging the outer surface of a first inner core member from the inner surface of the outer shell member; and
removing the first inner core member from the internal volume of the outer shell member to replace the first inner core member with the selected inner core member.

23. The method of claim 22, wherein the geometry of the at least one groove in the outer surface of the selected inner core member differs from the geometry of the at least one groove in the outer surface of the first inner core member.

24. The method of claim 13, wherein:
the outer shell member further comprises an inner shoulder;
each inner core member further comprises an outer shoulder; and
disposing the selected inner core member in the internal volume comprises engaging the outer shoulder and the inner shoulder to prevent expulsion of the selected inner core member from the outer shell member.

\* \* \* \* \*